United States Patent
Leary

(10) Patent No.: US 7,043,500 B2
(45) Date of Patent: May 9, 2006

(54) SUBTRACTIVE CLUSTERING FOR USE IN ANALYSIS OF DATA

(75) Inventor: James F. Leary, Galveston, TX (US)

(73) Assignee: Board of Regents, The University of Texas Syxtem, Austin, TX (US)

( * ) Notice: Subject to any disclaimer, the term of this patent is extended or adjusted under 35 U.S.C. 154(b) by 463 days.

(21) Appl. No.: 10/132,090

(22) Filed: Apr. 25, 2002

(65) Prior Publication Data

US 2003/0009470 A1    Jan. 9, 2003

Related U.S. Application Data

(60) Provisional application No. 60/286,833, filed on Apr. 25, 2001.

(51) Int. Cl.
*G06F 17/00* (2006.01)

(52) U.S. Cl. .................................... 707/104.1; 382/133

(58) Field of Classification Search ................ 707/1–7, 707/104.1; 702/179, 180; 382/168, 170, 382/181, 133
See application file for complete search history.

(56) References Cited

U.S. PATENT DOCUMENTS

| | | | |
|---|---|---|---|
| 5,199,576 A | | 4/1993 | Corio et al. |
| 5,204,884 A | | 4/1993 | Leary et al. |
| 5,550,058 A | | 8/1996 | Corio et al. |
| 5,703,964 A | * | 12/1997 | Menon et al. ............... 382/228 |
| 5,804,143 A | | 9/1998 | Leary et al. |
| 5,956,634 A | * | 9/1999 | Otterson et al. ............ 455/410 |
| 5,998,212 A | | 12/1999 | Corio et al. |
| 6,213,958 B1 | * | 4/2001 | Winder ........................ 600/586 |
| 6,260,038 B1 | * | 7/2001 | Martin et al. ................... 707/7 |
| 6,507,669 B1 | * | 1/2003 | Klassen ....................... 382/170 |
| 6,539,391 B1 | * | 3/2003 | DuMouchel et al. ........ 707/101 |
| 6,564,176 B1 | * | 5/2003 | Kremliovsky et al. ...... 702/189 |
| 2002/0091972 A1 | * | 7/2002 | Harris et al. .................. 714/47 |
| 2003/0199685 A1 | * | 10/2003 | Pressman et al. .......... 536/24.3 |
| 2004/0111408 A1 | * | 6/2004 | Caudill et al. .................. 707/3 |

FOREIGN PATENT DOCUMENTS

| | | |
|---|---|---|
| CA | 2106191 | 3/1992 |
| CA | 2107458 | 4/1992 |
| EP | 0 576 583 | 3/1992 |
| EP | 0 924 510 | 3/1992 |
| JP | 6507241 | 3/1992 |
| JP | 6507244 | 4/1992 |
| WO | WO 92/16829 | 3/1992 |
| WO | WO 92/17288 | 4/1992 |

OTHER PUBLICATIONS

Chiu, "Method and software for extracting fuzzy classification rules by subtractive clustering", IEEE 1996, pp. 461-465.*

Hung et al, "An easily implemented approach to fuzzy system identification", IEEE 1999, pp. 492-496.*

(Continued)

*Primary Examiner*—Uyen Le
(74) *Attorney, Agent, or Firm*—Mueting, Raasch & Gebhardt, P.A.

(57) ABSTRACT

A data analysis system and/or method, e.g., a data mining/data exploration method, using subtractive clustering is used to explore the similarities and differences between two or more multi-dimensional data sets, e.g., generated using a flow cytometer, an image analysis system, gene expression, or protein microarrays.

67 Claims, 10 Drawing Sheets

OTHER PUBLICATIONS

Tukey, John W., "Exploratory Data Analysis," Addison-Wesley, Reading, Massachusetts, 1977; 6pgs.

Van den Hove et al., "Multivariate Reconstruction of Lymphocyte Profiles in a Two-Dimensional Graphical Model as a Tool for the Investigation of Lymphocyte Subset Distribution in Health and Disease," *Cytometry,* 1997;28: 220-227.

Afifi et al., *Computer Aided Multivariate Analysis,* Can Nostrand Reinhold, NY 1990: 271-316.

Anderson, T.W., *An Introduction to Multivariate Statistical Analysis,* John Wiley and Sons, Inc., New York, 1984: 195-243.

Beck et al., "The Use of Relative Operating Characteristic (ROC) Curves in Test Performance Evaluation," *Arch Path Lab Med,* 1986; 110:13-20.

Choi, B.C.K., "Slopes of a receiver Operating Characteristic Curve and Likelihood Ratios for a Diagnostic Test,"*Am. J. Epidemiology,* 1998; 148(11): 1127-1132.

Hanley, J.A., "Receiver Operating Characteristic (ROC) Methodology: the State of the Art," *Critical Reviews in Diagnostic Imaging,* 1989; 29(3): 307-335.

Hokanson et al., "Some Theoretical and Practical Considerations for Multivariate Statistical Cell Classification Useful in Autologous Stem Cell Transplantation and Tumor Cell Purging," *Cytometry,* 1999; 36: 60-70.

Klecka, "Discriminant Analysis," *Sage University Paper series Quantitative Applications in the Social Sciences;* 1980: Series 07-019.

Kleinbaum et al., "Applied Regression and Other Multivariate Methods", PWS-Kent, Boston, MA 1992: 560-594.

Lachenbruch P.A., "Discriminant Analysis", Hafner Press, New York, NY 1975.

Leary, J.F., "Strategies for Rare Cell Detection and Isolation," *Methods in Cell Biology: Flow Cytometry;*1994; 42: 331-358.

Leary et al., "Isolation of Rare Cells by High-Speed Flow Cytometry and High-Resolution Cell Sorting for Subsequent Molecular Characterization-Applications in Prenatal Diagnosis, Breast Cancer and Autologous Bone Marrow Transplantation," Kluwer Academic Press, *Basic and Clinical Applications of Flow Cytometry,* Boston, MA 1996a; 271-318.

Leary et al., "New Methods for Detection, Analysis and Isolation of Rare Cell Populations," *SPIE (Journal of the Optical Society of America),* 1996b; 2678: 240-253.

Leary et al., "High Speed Cell Classification Systems for Real-Time Data Classification and Cell Sorting," *SPIE (Journal of the Optical Society of America),* 1997; 2982: 342-352.

Leary et al., "High Speed Real-Time Data Classification and Cell Sorting Using Discriminant Functions and Probabilities of Misclassification for Stem Cell Enrichment and Tumor Purging," *SPIE (Journal of Optical Society of America),* 1998a; 3260: 274-281.

Leary et al., "New High Speed Cell Sorting Methods for Stem Cell Sorting and Breast Cancer Cell Purging," *SPIE (Journal of Optical Society of America),* 1998b; 3259: 114-121.

Leary et al., "Real-time Multivariate Statistical Classification of Cells for Flow Cytometry and Cell Sorting: A Data Mining Application for Stem Cell Isolation and Tumor Purging," Part of the SPIE Conference on Advanced Techniques in Analytical Cytology III, San Jose, CA (Jun. 1999); published in *SPIE Optical Diagnostics of Living Cells II:* Jun. 1999; 3604: 158-169.

Leary et al., "Application of A Novel Data Mining Technique to Cytometry Data"; Slides shown at Optical Society Meeting on Optical Diagnostics of Living Cells (Jan. 2000).

Leary et al., "Application of New Novel Data Mining Technique to Cytometry Data" *SPIE Optical Diagnostics of Living Cells III:* Apr. 27, 2000; 3921: 84-89.

Leary et al., "Detection and Isolation of Single Tumor Cells Containing Mutated DNA Sequences" *SPIE Proceedings Systems and Technologies for Clinical Diagnostics and Drug Discovery II:* 1999a; 3603: 93-101.

McLachlan, G.J., "Discriminant Analysis and Statistical Pattern Recognition," John Wiley and Sons, Inc., New York, NY 1992: 7-9.

Rosenblatt et al., "A Theoretical Basis for Sampling Statistics Appropriate for the Detection and Isolation of Rare Cells Using Flow Cytometry and Cell Sorting," *Cytometry,* 1997; 26: 1-6.

Tatsuoka, M. M., *Multivariate Analysis: Techniques for Education and Psychological Research,* 2$^{nd}$ edition, New York, NY 1988: 18-62.

Adriaans et al., *Data Mining,* Addison-Wesley, Harlow, England 1994, 88 pgs.

Breiman et al., *Classification and Regression Trees,* Wadsworth International Group, Belmont, CA 1984, 370 pgs.

Fayyad et al., *Advances in Knowledge Discovery and Data Mining,* The M.I.T. Press, Cambridge, MA 1996, 630 pgs.

Jain et al., *Algorithms for Clustering Data,* Prentice Hall, Englewood Cliffs, NJ 1988, 334 pgs.

Jolliffe, I.T., *Principal Component Analysis,* Springer-Verlag, New York, NY 1986, 518 pgs.

Kennedy et al., *Solving Data Mining Problems through Pattern Recognition,* Prentice Hall, Upper Saddle River, NJ 1998, 400 pgs.

Swets et al., *Evaluation of Diagnostic Systems Methods from Signal Detection Theory,* Academic Press in Cognition and Perception, 1982, 138 pgs.

Weiss et al., *Predictive Data Mining: A Practical Guide,* Morgan Kaufmann Publishers, Inc. San Francisco, CA, 1998, 242 pgs.

* cited by examiner

SUBTRACTIVE CLUSTERING FOR USE IN ANALYSIS OF DATA

CROSS-REFERENCE TO RELATED APPLICATIONS

This application claims the benefit of U.S. Provisional Application No. 60/286,833, entitled "SUBTRACTIVE CLUSTERING FOR USE IN ANALYSIS OF DATA," filed Apr. 25, 2001, wherein such document is incorporated herein by reference.

STATEMENT OF GOVERNMENT RIGHTS

The present invention was made with support from the National Institutes of Health under Grant No. 5 RO1 GM38645. The government may have certain rights in this invention.

BACKGROUND OF THE INVENTION

The present invention relates generally to the analysis of data. More particularly, the present invention pertains to data mining of multi-dimensional data such as biological based data, e.g., flow cytometric data, microarray data, cell sorting data, imaging data, etc.

Analysis of multi-dimensional data presents various problems. For example, when using visualization to analyze such data, the viewing of multi-dimensional data as combinations of lower dimensional views (e.g., histograms and bivariate displays) results in the loss of information in an uncontrollable manner. Such loss of information frequently leads to loss of the pertinent information necessary to accomplish desired goals, e.g., isolation of cell subpopulations when analyzing flow cytometry data, loss of resolution in imaging applications, etc. For example, valuable information is lost when bivariate displays are reduced to a pair of uncorrelated histograms (e.g., representing data whose correlations between parameters are unknown).

Such loss of valuable information also occurs whenever multi-dimensional data is reduced to a collection of bivariate displays in an attempt to provide human visualization of higher dimensional data space. For example, when a 3D object (or data object) is projected down as a projection "shadow" onto a 2D plane, the shape of this projection shadow depends on the projection angle and may grossly distort the actual shape of the 3D object (or data object). While less immediately evident, the reduction of higher dimensional data space to 3D views, as is performed with various 3D renderings, is subject to the same problem, namely loss of information about the shape of the data objects in higher dimensional data space. Hence, while some reduction of dimensionality may be required to produce human visualizable 2-D and 3-D displays, the conventional process of displaying all possible combinations of bivariate displays only provides one human visualizable viewpoint and is subject to distortions which range from slight to major distortions, depending on how the data is projected down onto a lower dimensional surface (e.g., plane).

Multivariate statistics offer us various data analysis alternatives (e.g., principal component analysis (PCA) or discriminant function analysis (DFA)) which give additional viewpoints and projection of multi-dimensional data. For example, PCA and DFA, along with interactive 3-D displays, have been used to select better projection angles for less distortion than simple collections of bivariate views of the data to provide optimal analysis parameters for sorting gates in flow cytometry systems. Such interactive 3-D visualization can be used to provide for conventional cluster analysis, e.g., whereby data clusters can be identified in multi-dimensional data space and intelligent starting values for the clusters can be provided as inputs for a guided cluster analysis. However, such data analysis frequently requires human visualization of multi-dimensional data in order to determine the appropriate number and/or location of clusters which can be difficult even with the aid of a multivariate statistical methods such as DFA and PCA. Ultimately, there is need for a data analysis method which does not require human visualization methods nor direct human supervision of multi-dimensional data analysis.

In addition to a need for improved data analysis, there is a need for ways of comparing multi-dimensional data sets (e.g., test and control multi-dimensional data sets) and providing knowledge discovery which can point out the important differences or similarities between the two or more multi-dimensional data sets without direct human intervention. Such methods of knowledge discovery can be referred to generally as data mining. In other words, data mining generally refers to any set of methods or apparatus that look for meaning in data as opposed to merely manipulating or performing computations on the data. Meaning in data basically refers to anything that helps to guide one skilled in the art to what is important or significant about the data, or suggest an approach for further analysis of the data.

Conventional clustering is one type of data mining method. Conventional clustering usually involves computation of distances between data points in multi-dimensional space. Generally, assignment of a given data point to a cluster is usually done by a least squares, or other, minimization method (e.g., minimization of distances from the centers of clusters) which either ignores correlations between the parameters of a data point (e.g., such as in K-means clustering) or tries to take these correlations into account (e.g., such as in Mahalanobis clustering). Such procedures when dealing with multi-dimensional data are very computationally intensive. For example, it is computationally challenging to cluster multi-parameter flow cytometric data including more than about 50,000 cells. As such, this makes cluster analysis difficult or even impossible to perform on rare cell subpopulations (i.e., as used herein rare subpopulations are present at a percentage in the range of about 1.0% to 0.0001%) which require data sets containing many millions of cells (e.g., data points) to obtain enough rare cell data. Necessarily, the rare cells still tend to be sparse in their distribution in higher dimensional data space; one of the features of the so-called "tyranny of dimensionality further described below.

Data mining is of particular interest in flow cytometry/cell sorting applications. For example, the general problem of cell sorting is to identify cell subpopulations of interest and to isolate them. Typically, the usual technique is to display various histograms and bivariate views of the full cytometric data obtained from running a sample of cells through a flow cytometer. One skilled in the art then uses human pattern recognition to identify cell subpopulations of interest. Through interactive 2-D displays, various regions are manually set by the one skilled in the art. These regions can then be combined through appropriate Boolean logic to set a gate which is then used as a sort decision boundary in a cell sorting process.

Under simple circumstances, this procedure is adequate to sort the cells of interest. However, the method suffers from various shortcomings. First, in order to provide human visualization on a 2-D computer system, the multi-dimensional data is reduced to simple histograms and bivariate displays as described previously herein. Higher dimensional data is projected down onto these 2-D displays, losing valuable information about the cell subpopulations that was available, but not readily visualizable in the original multi-dimensional data space. Second, the choice of regions and sort gates is usually arbitrary and subject to individual experimenter expertise and prejudices.

Many flow cytometry applications require the measurement and sorting of small subpopulations of cells (or other objects/particles) from large populations. These applications require a multi-dimensional/high resolution flow cytometry experiment and often produce data sets in which the data do not always cluster into discrete subpopulations amenable to visual pattern recognition or to conventional cluster analysis techniques.

Flow cytometric data, e.g., both flow and image cytometric data, include a large number of sets of measurements taken on single cells. This multi-parameter data on populations of single cells defines a multi-dimensional data space where there tend to be some natural groupings of multi-dimensional data points which mirror the similarities of cells belonging to particular cell subpopulations. While the multi-dimensional data points do show some grouping, the probability for all of the measurements being identical for even two cells within the measurement resolution (e.g., 8-bit to 12-bit resolution for each measurement) is very small. Hence, any groupings depend on some index, typically a multi-dimensional distance metric, to classify two cells within a similar group or cluster.

Over the years, classification of cells from rare and complex cell populations have utilized a wide variety of classifier systems such as multi-dimensional cluster analysis. However, methods such as conventional cluster analysis, 3-D visualization techniques, guided cluster analysis, and fuzzy clustering routines are, computationally intensive as described above.

In many flow cytometric data sets, the data do not cluster into discrete subpopulations that can easily be identified by human pattern recognition. To satisfy both the demands for very large data sets and amorphous data structure, rapid pre-classification techniques have been used.

Although cluster analysis methods have been developed over the years to perform this grouping of cells into cell subpopulations, a more complex problem of comparing clusters between different data files is evident. While clustering data points within one data file is certainly of interest, comparison of data between samples (e.g., treated versus untreated controls, cancer versus normal cells, etc.) is of even heightened importance.

Generally, what one skilled in the art would like to know is what is different between two cell samples. That question necessitates comparing the clusters within two separate data files. Since cluster positions can vary slightly, which is a common problem encountered in this situation, measures of similarity or dissimilarity need to take such variation into account. Due to the scarcity of data points in multi-dimensional data space, a much more complex analysis than a simple difference spectrum is required for comparison of the multi-dimensional data sets. This is particularly the case since data points in different data sets are typically only similar, and not exact.

In other words, in general, an illustrative problem when dealing with flow cytometric data is to take two data sets, the first with cell population "A" and the second with the populations "A and B," analyze such data sets, and then produce the data set with population "B" only. Clearly, the way to obtain "B" only is to subtract the "A" only data set from the "A and B" data set.

Such subtraction has previously been accomplished by others at the single parameter histogram level. However, extension of this method from single parameter histogram data to multi-dimensional data is complicated for various reasons. Such complications arise because the data is both multi-dimensional and high resolution. Attempting to deal with the data as a multi-dimensional array leads to severe storage and computational problems.

Traditionally, such situations dealing with multi-dimensional arrays have been called "the tyranny of dimensionality". The rational for this tyranny is evident. For example, simple numerical integration in "n" dimensions requires $k^n$ terms in the sum, where k is the number of division points on each axis (e.g., bit resolution in digitized data); integration must be numerically performed to compute probabilities. For example, if the dimension of the data set (i.e., the number of variables of a multi-dimensional data set being measured) is 10, and each axis is divided into 1,000 intervals, then the number of terms is $1,000^{10}$ (i.e., $10^{30}$). As can be seen, this is a very large number of array elements.

Typically, when dealing with flow cytometric data, this tyranny of dimensionality has been addressed by reducing the resolution of the data. For example, multi-parameter 10-bit data (i.e., 1,024 channels) is typically expressed as a 6-bit×6-bit (i.e., 64×64) channel scattergram. For three-dimensional data displays, the data resolution is typically reduced to 5-bit (i.e., 32×32×32) channels. For two-dimensional data display/analysis for 10-bit or 12-bit data, a large amount of loss and resolution of the original data may be acceptable. However, for higher dimensional data display/analysis, a continued reduction in dimensionality will start squashing the data into such large channel bins that all resolution of different subpopulations is lost; effectively merging all of the data into a few meaningless clusters of data.

In other words, the size of the data arrays as described above expands exponentially with dimensionality. As such, a single parameter histogram at 10-bit resolution generates a data set of only 1,000 array elements, a three-parameter measurement at 10-bit resolution requires $10^9$ elements, and a five-parameter measurement at 10-bit resolution requires $10^{15}$ elements. Thus, array element subtraction of the multi-dimensional data sets becomes problematic in terms of data storage and data processing cycle times.

In summary, although the subtraction problem has been addressed in simple bin to identical bin subtraction of histogram data, applying similar subtraction techniques to multi-dimensional data quickly becomes daunting due to both the exponential scaling of multi-dimensional data by the number of dimensions, and also due to the tyranny of dimensionality as described above whereby the data points become sparse and unique in multi-dimensional data space, such that no two points in similar clusters in two or more data sets are numerically identical.

As described above, although the subtraction problem has been addressed in some multi-dimensional applications by reducing the resolution of each data set, reduction of the data array to a computationally manageable size sacrifices resolution to the point where in a multi-dimensional data experiment, the data is merged into few and meaningless clusters and the ability to detect a subpopulation of cells is lost. Further, conventional clustering algorithms are computationally intensive and thus do not solve the problem of retaining resolution while reducing computational intensity, e.g., a problem readily apparent in analysis of multi-dimensional flow cytometric data. In addition, because the current methods are computationally intensive, they are prevented from being employed on lower performance computer platforms.

No current methodology is known in the flow cytometry field which can preserve the information content of multi-dimensional high resolution flow cytometric data, and thus capitalize on its inherent ability to measure and sort cell populations while reducing computational intensity to a manageable size compatible with cytometry hardware and analysis/sort cycle times. Further, there is no methodology in use for other fields which operate on two or more multi-dimensional data sets (e.g., imaging data or microarray data for genomic or proteomic experimentation) which can provide such data analysis while reducing computational intensity.

Additionally, current genomic and proteomic multi-dimensional data contains mixed data types containing different scaling factors (e.g., linear of log digitized micro-array spot intensities correlated to categorically identified human gene or protein names or signal transduction pathways). Conventional clustering algorithms find it difficult to compute distances with mixed data types with different scaling factors.

SUMMARY OF THE INVENTION

The present invention provides a data analysis (e.g., data mining) system and/or method which does not require human visualization methods nor direct human supervision of multi-dimensional data analysis. Further, at least in one embodiment, the present invention is a way of dealing with sparse data spaces by using data events, normalized over a multi-dimensional sub-region of space, subtracted and re-binned according to different algorithms to best reconstruct the remaining subtracted data points in a manner such that this subtracted data can be visualized or further analyzed by other methods.

Yet further, the present invention recognizes that subtraction in analysis of multi-dimensional data requires more sophisticated measures to analyze similarity or dissimilarity to decide whether a data point in one data set should be subtracted from a similar (numerically, or by some non-numeric measure) but different data point in a different data set. In other words, the present invention takes into consideration that data points in different data sets need only be similar (e.g., not numerically identical) to be compared (e.g., subtracted), whereby such similarity can be defined by the user.

In one embodiment of the present invention, a data analysis system and/or method, e.g., a data mining/data exploration method, is used to objectively identify data subsets of interest within a data file (subtract a control file data set from a test file data set) or to explore the similarities and differences between two or more data files of multi-dimensional data sets. For example, such a method may be applied to data generated using a flow cytometer, an image analysis system, gene expression, or other system such as those using microarrays.

Generally, the present invention involves grouping the data of multi-dimensional data sets in multi-dimensional space and then comparing those groups with groups of data in one or more additional data sets. As such, the groupings become data objects, and the technique involves various measures of similarity between data objects in different data sets.

The data mining technique according to the present invention is referred to herein in many instances as "subtractive clustering" because it provides a type of exploratory data mining analysis of the differences between, as opposed to within, two or more data sets. This subtractive clustering data mining technique does not involve conventional, computationally-intensive, numerical cluster analysis techniques but is referred to as clustering because, at least in one embodiment, it first groups or clusters data into data objects for one data set and then compares it with similarly defined data in another data set. The present invention minimizes computational intensity while retaining multi-dimensional measurement resolution and can use or deal with mixed data types.

For example, instead of assigning the individual data points to traditionally defined clusters as in conventional cluster analysis, the data of a first data set is subdivided into smaller groups. The data of one or more other multi-dimensional data sets are similarly grouped into similar (e.g., nearest neighbor, or region-averaged) data points which are subtracted from the data points of the groups of the first data set; the remaining data points being re-binned so that they form a data subset of the original data sets. The re-binned data can then be re-displayed or reanalyzed by subtractive clustering or by other data analysis methods, if desired, in a manner similar to the original data. This subtraction is not a simple subtraction of equal data points since virtually no multi-dimensional data points are the same on the basis of all measured parameters. Instead, similar multi-dimensional data points are subtracted from each other, whereby a variety of algorithms can be used to define what the user (e.g., researcher) considers similar.

One data mining method according to the present invention includes providing a plurality of data points for at least a first multi-dimensional data set of the two or more multi-dimensional data sets. Each data point is representative of at least two parameters associated with an event of a plurality of events. The plurality of data points are grouped into one or more multi-dimensional groups of clustered data points with each of the one or more multi-dimensional groups being defined by one or more bin boundaries associated with the at least two parameters. A plurality of subtraction data points are provided for at least a second multi-dimensional data set of the two or more multi-dimensional data sets. Each subtraction data point is representative of the at least two parameters associated with an event of a plurality of events. The plurality of subtraction data points are also grouped into one or more groups of subtraction data points but such groups are based on the one or more bin boundaries of the one or more multi-dimensional groups of clustered data points. As such, each of the one or more groups of subtraction data points corresponds to one of the one or more multi-dimensional groups of clustered data points. The plurality of subtraction data points of one or more groups of subtraction data points are compared to corresponding multi-dimensional groups of clustered data points to determine similarities or differences therebetween.

In one embodiment, such a comparison includes subtracting at least a plurality of the subtraction data points from similar, not necessarily identical, data points of the corresponding multi-dimensional groups of clustered data points.

A system to implement the data mining method is further provided.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

The present invention will be further described with reference to the drawings, wherein.

DETAILED DESCRIPTION OF THE EMBODIMENTS

Figure 1:
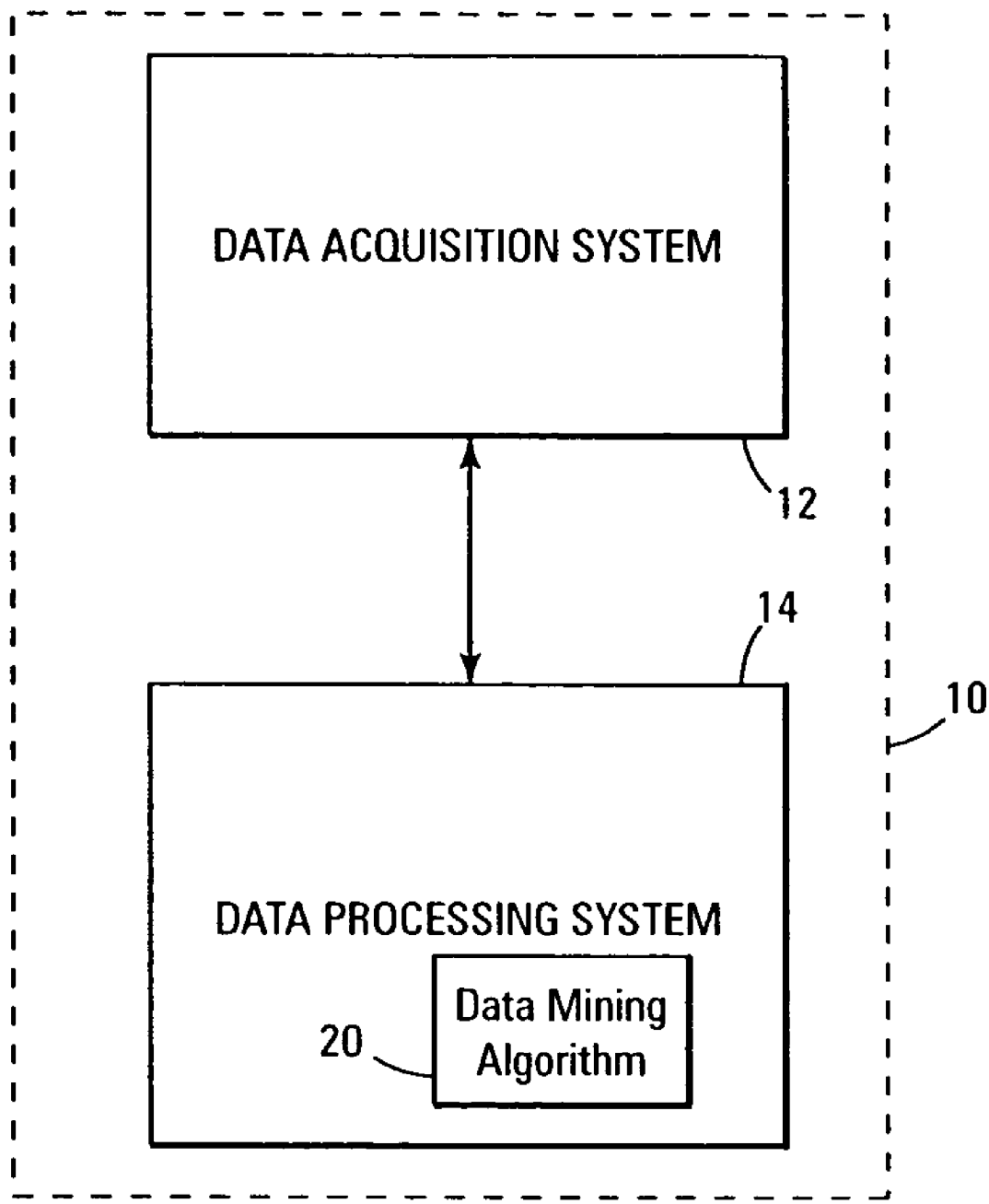
FIG. 1 is a block diagram of an application-specific system employing a data mining methodology according to the present invention.

FIG. 1 is a simplified block diagram of an application-specific system 10 employing subtractive clustering according to the present invention. The application-specific system 10 includes a data acquisition system 12 in communication with a data processing system 14. The data processing system 14 is operable on multi-dimensional data using the data mining algorithm 20, e.g., a subtractive clustering algorithm. It is possible, for example, to embed the algorithm in a real-time data classification system or even use it to provide real-time physical cell sorting decisions.

Generally, the application-specific system 10 involves comparing clusters of data points occurring in two or more multi-dimensional data sets to reveal the differences or similarities between such multi-dimensional data sets. Such comparisons using subtractive clustering algorithms and methods of the present invention are applicable to a wide variety of multi-dimensional data sets and data types acquired with use of the data acquisition system 12, e.g., a flow cytometer system, an imaging system, a microarray imaging system, etc.

Such multi-dimensional data sets include multi-parameter data, including mixed data types, from many different fields, representative of at least two parameters associated with each of a plurality of events. For example, with respect to flow cytometric data, each cell may be considered an event with multiple parameters such as cell volume, fluorescence, light scatter, etc. being measured. Further, for example, for microarrays (e.g., DNA chips), each gene fragment, protein fragment or spot of the microarray may be an event for which a plurality of parameters are measured. Yet further, for example, for a multi-spectral image, each pixel may be an event for which a plurality of parameters are measured. Therefore, as used herein, an event may be defined as anything for which multiple parameters are measured. As such, as used herein, multi-dimensional data sets may also be referred to as multi-parameter data sets.

Subtractive clustering according to the present invention is particularly useful with respect to flow cytometric data sets as further described herein. However, such data analysis can be used for a wide variety of applications in addition to data analysis of flow cytometric data. For example, subtractive clustering according to the present invention may be used for analysis of image data, e.g., multi-dimensional image data such as multi-spectral imaging data.

Further, for example, since the subtractive clustering techniques according to the present invention can be used with mixed data types, they can be applied to the analysis of various types of microarray data or, for example, in other computationally intensive biological applications in which one is searching for small differences between multi-dimensional data sets which may be large and computationally challenging. For example, the present invention may be applicable to microarray data (e.g., gene expression) data which not only includes the numerical data from fluorescence or phospho-imaging signals, but also includes related data associated with gene identity and other knowledge specific to each microarray spot. For example, in such circumstances, a search may be conducted for small differences between data sets in the measurement of differential gene expression from data sets produced either by nucleic acid and protein microarrays, as well as differences between two or more images, either conventional 2-D or 3-D images, or in more complex multi-dimensional images such as spectral imaging data.

Microarray gene expression analysis is well-suited for extensive data mining, such as with the use of subtractive clustering according to the present invention. Gene expression measurements may require application of a clustering algorithm in that one is either searching for genes of similar function based on similar expression patterns, or differences in gene expression after perturbation to the organism, to determine which biochemical pathways are involved in the perturbation.

In other words, the subtractive clustering techniques may be applied to multi-dimensional data sets that as described herein may take various forms. For example, the multi-dimensional data sets (e.g., test and control data sets) may include not only data generated by flow cytometry analysis, but also heterogeneous data such as phenotype data for a sample being run. Further, the subtractive clustering algorithms may be used in image analysis and multi-spectral imaging. Yet further, the multi-dimensional data sets may be generated by microarray analysis of gene expression as in the field of genomics, with each event, for example, representing a specific gene or gene fragment. Still further, the multi-dimensional data sets may be generated by two dimensional (2-D) or three dimensional (3-D) gels or other analyses of protein expression as in the field of proteomics, with each event, for example, representing a specific protein or a protein fragment. Yet further, the multi-dimensional data sets do not necessarily just include data generated by microarray analysis of gene or protein expression, but also may be heterogeneous data such as phenotype (e.g., gene-identifying or protein-identifying) data for a sample being run.

With respect to subtractive clustering using flow cytometry data (e.g., subtracting multi-dimensional control data sets from a test multi-dimensional data set to allow detection of the differences between the two multi-dimensional data sets), various uses for such subtraction are known. For example, subtractive clustering may be used in the sorting of a cell subpopulation (e.g., sorting of a subpopulation of stem cells from a population of differentiated cells, with purging of tumor cells prior to use of sorted stem cells in transplantation). Further, for example, subtractive clustering may be used in the sorting of a subpopulation of cancerous cells from a normal cell population prior to gene expression profiling measurements on the cancerous cells to determine perturbations to biochemical pathways in cancer. Further, high throughput screening of large cell libraries may be performed using subtractive clustering according to the present invention.

Yet further, subtractive clustering may be used for sorting subpopulations of cancerous cells obtained before and after chemotherapy. The sorting of cell populations of cancerous cells obtained before and after chemotherapy requires multiple subtractions as one must first subtract a control (i.e., normal cells) data set from both the pre-treatment and the post-treatment multi-dimensional data sets. This leaves data sets containing cells potentially of interest. One then subtracts the cells of potential interest for the post-treatment data set from the cells of potential interest for the pre-treatment data set to determine the change in biochemistry due to the treatment. The result is the actual cells of interest.

Analysis of data can also be performed on similar data from nonbiological objects such as microbeads on which chemistries can be performed and screened. For example, such analysis may be important in high throughput screening of combinatorial chemistry libraries for drug discovery.

Many of the above uses for subtractive clustering applied to the above mentioned multi-dimensional data sets are offline data analysis applications. However, the results of subtractive clustering can also be used for real-time applications. For example, and clearly not limited to this particular application only, the results of subtractive clustering can be used to set sorting decision boundaries for cell sorting, for physical isolation of cells or other objects, either as subpopulations or as single cells or objects.

Of particular benefit is the subtractive clustering method and its ability to objectively detect small cell populations from multi-dimensional data sets (e.g., rare cell subpopulations which are defined herein as being present at a percentage in the range of about 1.0 percent to 0.0001 percent). Such detection of small cell subpopulations does not sacrifice the inherent resolution of each parameter measurement of the multi-dimensional data sets, and is compatible with computational performance of flow cytometry hardware as has been previously demonstrated. Further, such objective detection of small cell subpopulations has a reasonable cycle time and is valuable in allowing real-time sorting decisions to be made.

Most of the applications of the subtractive clustering methods described above involve application of the subtractive clustering techniques to raw multi-dimensional data sets. However, subtractive clustering according to the present invention may also be applicable to data sets which have been transformed by known methods for reducing data dimensionality such as, for example, PCA, DFA, logistic regression analysis (LRA), projection pursuit (PP), or other multivariate statistical classifiers. For example, subtractive clustering could be used to show which of these data analysis methods works best for a particular data set.

Further, the data mining subtractive clustering algorithm 20 described herein can be used to improve functionality of subsequent analyses by other more traditional cluster analysis and other data analysis programs. Subtractive clustering according to the present invention is powerful in that while taking into account the correlation of multiple parameters, no assumptions are made about either parametric relationships or data types. Traditional cluster analysis can be viewed as a synergistic partner to subtractive clustering as described herein by combining the technique of binless classification of the subtractive clustering program with such methods as principal component biplot analysis and the various channel-by-channel histogram subtraction methods that are known in the art.

The technology described herein may be used in various types of research, such as, for example, pharmaceutical, biotechnology, medical device industries, and also used by researchers involved in, for example, stem cell research, cancer research, infectious disease research, preparation of cells (e.g., isolation of desired cells with the purging of tumor cells) to be used in transplantation, drug discovery, and development and utilization of gene expression measurements.

Generally, flow cytometry and microarray analysis are two major enabling tools used in such technology fields. A third analysis type involves nucleic acid and peptide sequencers. Although various applications have been listed above, it will be apparent to one skilled in the art that any application involving multi-dimensional data sets may benefit with use of the subtractive clustering according to the present invention.

Figure 10A:
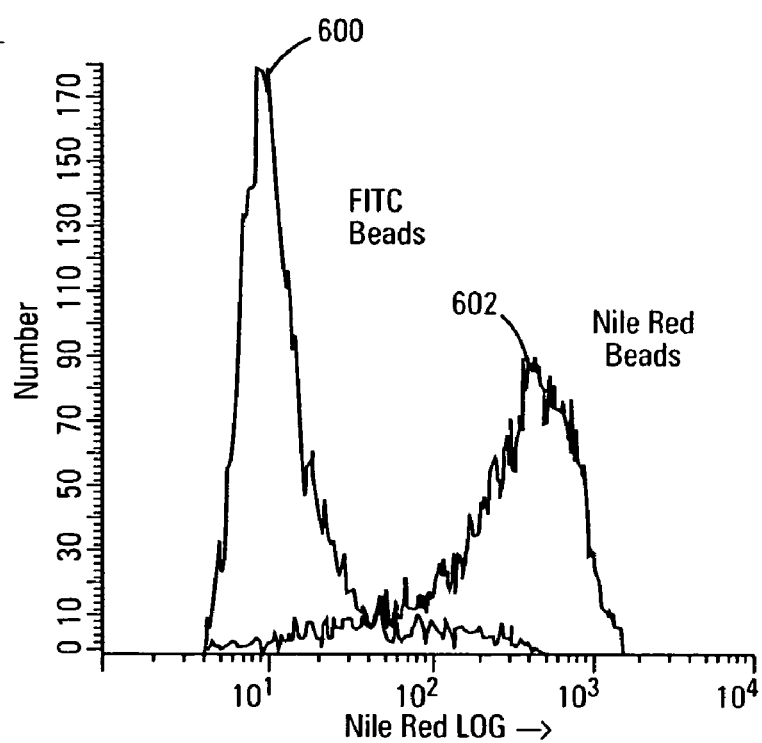
FIG. 10 illustrates a comparison of a distribution of raw data versus subtractive cluster analysis data resulting from a subtractive clustering analysis method according to the present invention for one illustrative example of subtractive clustering according to the present invention.
Figure 10B:
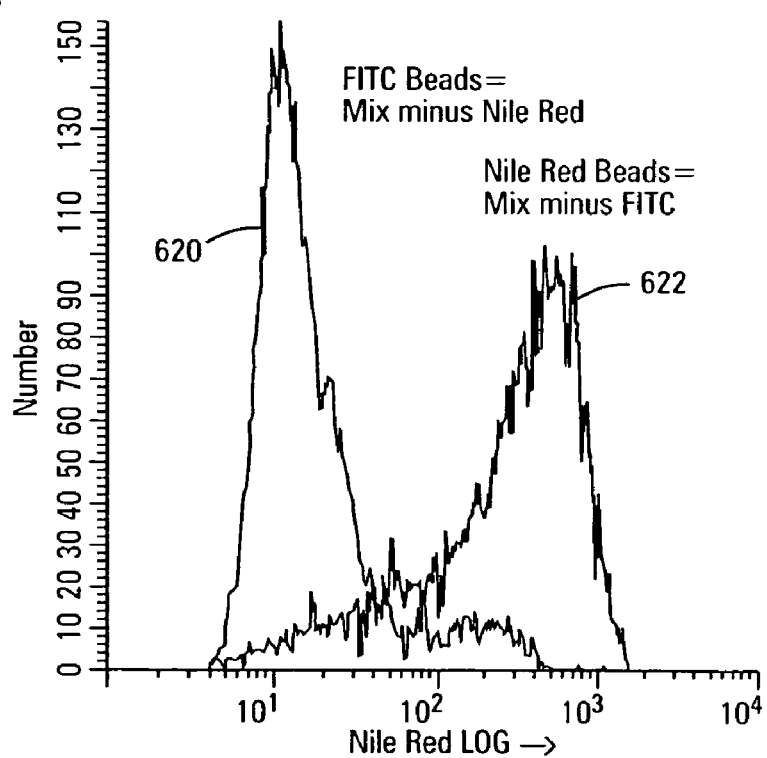

The data processing system 14 of the application-specific system 10 may include any conventional performance computer platform operable under control of data analysis routines including the subtractive clustering routines described in detail herein. The subtractive clustering data mining algorithm 20 compares the similarities and differences between two or more data files, e.g., test and control data files, provided to the data processing system 14 either through the use of data acquisition system 12 or any other manner such as through external memory, stored data, downloaded files (e.g., look-up tables), embedded algorithms on digital signal processing (DSP) boards or similar boards, etc. The present invention may be used, implemented, and/or partially implemented with one or more available software routines or programs. For example, the outputs of the present invention may be used with Boolean logic gating within the commercially available WinList™ 4.0 for Microsoft Windows 95/NT™ (Verity Software House, Inc., Topsham, Me.) as shown in FIG. 10.

As the computational requirements are reduced using the present subtractive clustering techniques described herein, the multi-dimensional data sets can be analyzed on conventional computer platforms including personal computers. For example, it will be readily apparent to one skilled in the art that the present invention may be adapted to be operable using any bit processor-based system, e.g., a personal computer operating in a Windows or Windows NT environment, and, further, that the present invention is in no manner limited to any particular processing system. The amount of memory in the system should be sufficient to allow for operation of the program 20 and storage of data, such as the multi-dimensional data sets and results therefrom. It is readily apparent that such a memory may be provided by peripheral memory devices including those used for implementing embedded systems on DSP or similar boards.

The data processing system 14 may include any number of other peripheral devices as desired for operation of the system 14, such as, for example, the following respective devices: display, keyboard, mouse, etc. However, one skilled in the art will recognize that the system is in no manner limited to use of such devices, nor that such devices are necessarily required for operation of the system.

The data mining subtractive clustering algorithm 20 allows for subtractive clustering of data between files of varying sizes and permits the analysis of very large files. Various controllable parameters in the program allow for definition of similarities in the data clusters in multi-dimensional space (e.g., controllable by user selected input via a user interface such as that shown in FIG. 7). Subtraction is not a simple subtraction of multi-dimensional data points, but rather a subtraction of similar data points which may or may not have the same data values. Data points in multi-dimensional space need not be identical numerically, as this is rare. Data points con be considered "similar" and then subtracted from one another to provide a subtractive clustered subset of the original data. In this manner, the present invention is distinguishable from other conventional methods which typically only allow comparison of numerically identical data points.

In addition, since the multi-dimensional coordinates of each data point are not stored in a multi-dimensional array, the program is not limited by data dimensionality or resolution. Data are processed from listmode data into sublists that permit rapid comparison between multi-dimensional data sets (e.g., test and control files). By utilizing a Windows interface, such as will be described further in detail below with reference to FIG. 7, the input of an experienced researcher having pertinent information concerning the number of biological relevant cell subpopulations within a mixed sample can be taken into account.

The data acquisition system 12 of the application specific system 10 may be any acquisition system that would result in any of the multi-dimensional data sets as described herein upon which subtractive clustering may operate. For example, the data acquisition system may include a spectral imaging system, a flow cytometry system, a microarray imaging system, an optical system used to measure parameters, one or more sensors or detector used to measure parameters, or any other data acquisition devices known in the art for providing one or more parameters for a plurality of events. One skilled in the art will recognize that numerous available systems provide multi-dimensional data sets that may be operated on by the subtractive clustering algorithm and that the present invention is not limited to any particular type of multi-dimensional data sets or acquisition systems.

Although the present invention is not limited to any particular multi-dimensional data sets, as described in detail below, the present invention is particularly beneficial for data analysis of flow cytometric data. As such, and for simplicity reasons, the present invention shall be described further herein with particular detail with respect to analysis of cell data as may be provided by a flow cylometry system. A cell represents an event for which multiple parameter measurements are performed. However, as previously described herein, the present invention is not limited in any manner to operation upon only cell data.

Figure 2:
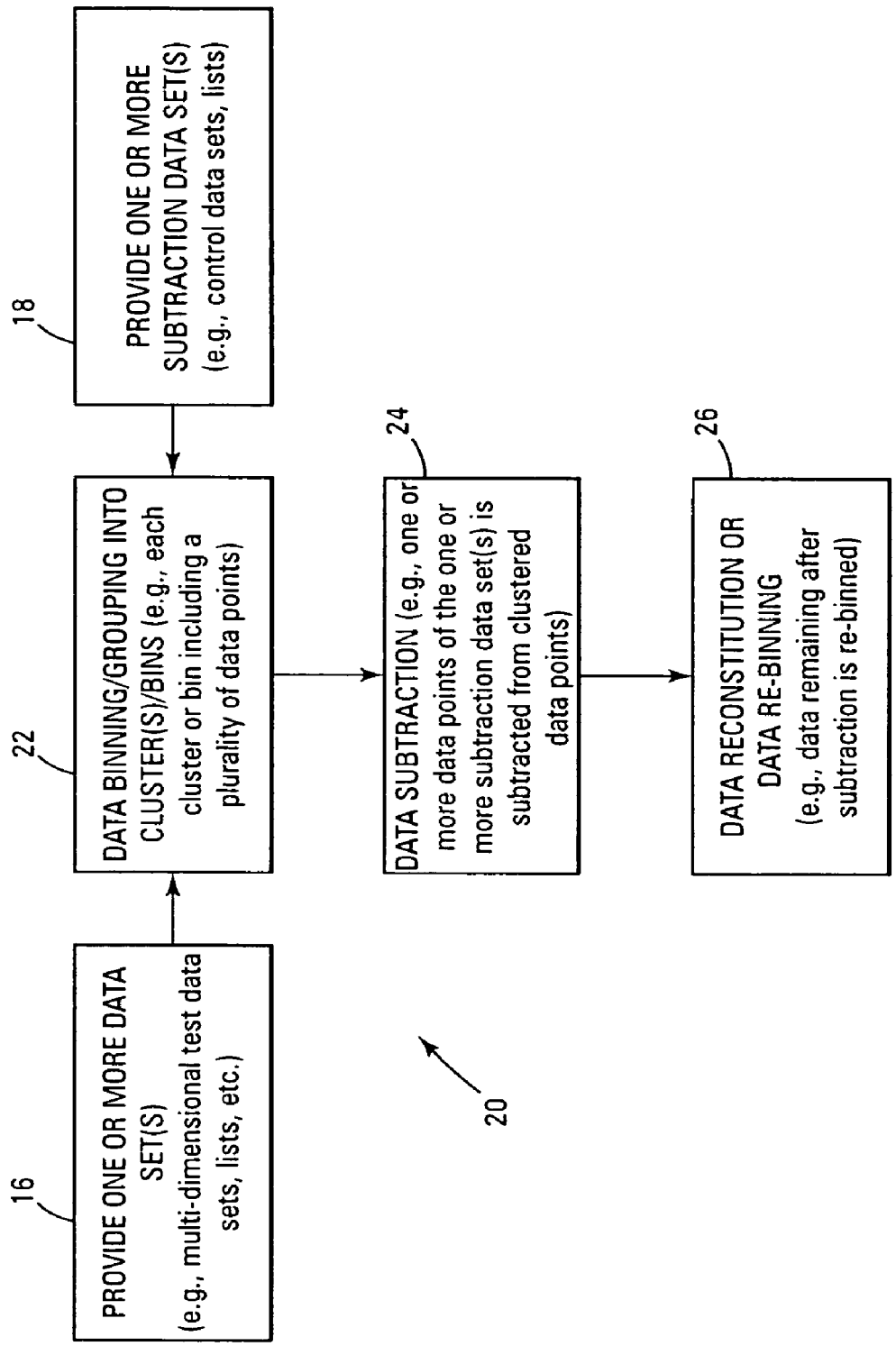
FIG. 2 is a flow diagram of a subtractive clustering method for use in data mining according to the present invention.

FIG. 2 generally shows a flow diagram of an illustrative embodiment of a subtractive clustering algorithm or method 20 according to the present invention. Unlike most other conventional clustering algorithms or methods which cluster the data of only one data set without reference to other data sets, the subtractive clustering method 20 operates on two or more multi-dimensional data sets.

As shown in block 16, one or more multi-dimensional data sets is provided for grouping by the subtractive clustering method 20. For example, the one or more multi-dimensional data sets may be flow cytometric data as previously described herein, such as a test file data set. For simplicity and ease of understanding, the remainder of the present description shall primarily be described with use of a test file data set provided per block 16. However, it will be recognized that more than one data set may be used, that the data file may not necessarily be a file containing test data, and that the description provided herein may be extended to cover operation on multiple data sets and other types of data.

Likewise, one or more subtraction multi-dimensional data sets are provided per block 18. For example, the one or more subtraction data sets may include control data sets. Once again, for simplicity and ease of understanding, the remainder of the present description shall primarily be described with use of a control file data set (e.g., subtraction data set) provided per block 18. However, it will be recognized that more than one data set may be subtracted from the data set provided per block 16, that the data file may not necessarily be a file containing only control data, and that the description provided herein may be extended to cover operation on multiple subtraction data sets and other types of data besides control data.

With the multi-dimensional test data set provided in block 16 and the multi-dimensional subtraction data set provided as shown in block 18, the data sets are compared using the subtractive clustering method 20 to measure similarity or dissimilarity therebetween. For example, if a multi-dimensional test data set is provided in block 16 and a control data set is provided as the subtraction data set per block 18, the result of the subtractive clustering method 20 may be a difference data subset resulting from the subtraction of the control data set from the multi-dimensional test data set.

Generally, the subtractive clustering method 20, at least in one embodiment, includes the following algorithmic processes. First, data binning/grouping into cluster(s)/bins is performed (block 22). In data binning block 22, for example, the rapid determination of regions of higher population density, or in other words clusters of data within a multi-dimensional space, is performed.

Generally, the multi-dimensional test data set provided per block 16 and another data set (e.g., the subtraction data set or control data set) provided via block 18 are binned or grouped as will be further described below. For example, the grouping or binning of data points of the test data set will result in groups (e.g., clusters) of a plurality of data points or coordinates, e.g., clustered weighted data points. The groups are preferably multi-dimensional groups (e.g., clusters) defined by one or more bin boundaries associated with at least two parameters measured for each of the plurality of events (e.g., cells).

Further, for example, the data points of the subtraction or control data set are binned or grouped based on the defined bin boundaries for the groups of clustered test data points or coordinates. In other words, at least in one embodiment, the control data points are grouped into groups having bin boundaries that are the same as the bin boundaries generated for the grouping of the test data points. Like the grouping of the test data points, the grouping or binning of control data points of the control data set will result in groups (e.g., clusters) of a plurality of control data points or coordinates, e.g., clustered weighted data points.

As the subtraction (e.g., control) data points are grouped based on the bin boundaries defined for the groups of test data points, each group of control data points can be compared to the respective group of test data points having corresponding bin boundaries. In other words, similarly defined groups of data points can compared to one another. It will be recognized that, as used herein, the terms group and cluster are used interchangeably in many instances.

With at least the multi-dimensional test data set (e.g., provided per block 16) grouped into one or more multi-dimensional groups of clustered data points, and with the plurality of subtraction data points (e.g., provided per block 18) grouped based on the bin boundaries of the grouped test data, data subtraction (block 24) can be performed to compare the groups of subtraction data points to the one or more multi-dimensional groups of clustered test data points to determine similarities or differences therebetween. The data subtraction, for example, may provide for minimization of a set of control array elements based on knowledge of cluster density within the multi-dimensional space of the test data set determined in data binning and subtraction of similar, but not necessarily identical, control data points from test data points of the multi-dimensional groups of clustered data points.

After the subtraction is completed (block 24), the result of the subtraction is re-binned in data reconstitution block 26. In other words, after subtraction of the control data points from the test data points of the multi-dimensional clusters, the results (e.g., a difference data set) are re-binned so that they can be re-displayed in a similar manner or new view of the data, re-analyzed, or otherwise used as a subset of the original data set. Alternatively, the re-binned subset of data resulting from the subtractive clustering algorithms can be processed again by subtractive clustering (e.g., using a sub-region normalization before subtracting), or by a different analysis procedure.

In operation, to begin the subtractive clustering method 20, at least two multi-dimensional data sets are required. Although more data sets may be used, for simplicity as described above, more detail with regard to the subtractive clustering method 20 shall be provided with respect to the subtractive clustering of the test file data set provided via block 16 and the control file data set provided via block 18, e.g. the subtraction data set. In other words, the control file data set is to be subtracted from the test file data set, but this process can be continued with additional data files (e.g., in an iterative process to explore in greater depth subsets of the originally considered data, or of additional controls).

For example, the two data files may be a positively stained sample data file and a background control sample data file. One skilled in the art will recognize that various other examples of data sets may be used as previously described herein in various different applications. For example, several other data set examples include data sets where cells in one data file are perturbed by some agent and the control data file represents unperturbed cells, or even three data files such as cancerous cells prior to chemotherapy and afterwards, and comparison of these two data files with one data file containing normal cells. The capability to explore the relationships between more than two data sets is advantageous in many applications.

Figure 3:
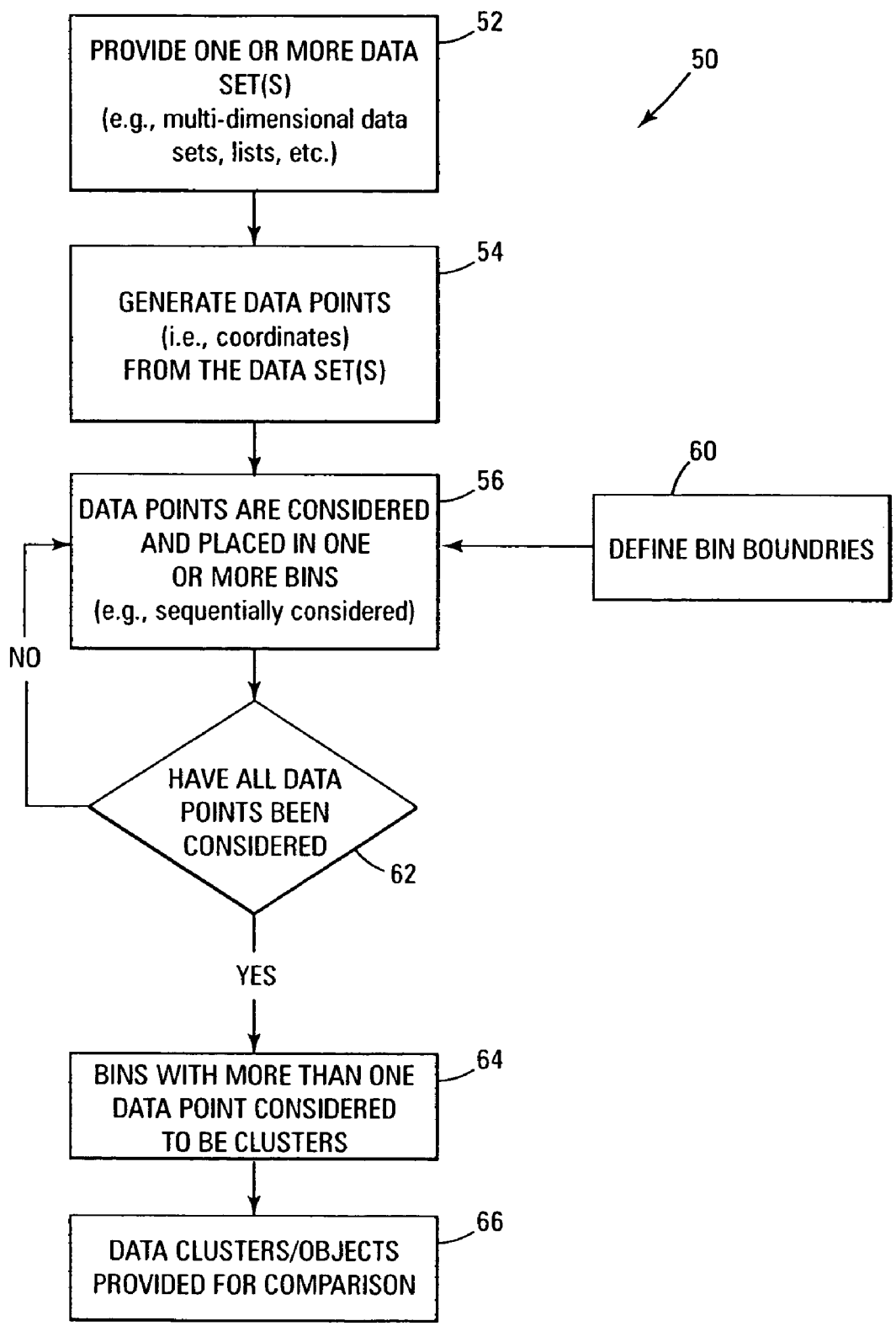
FIG. 3 is a flow diagram of an illustrative data binning method for use in the subtractive clustering method shown generally in FIG. 2.

With the test file data set and the control file data set provided (e.g., flow cytometry standard (FCS), a field and industry file format standard, formatted test listmode data files), data binning (block 22) is performed. One exemplary embodiment of a data binning method 50 for the test data set is shown in FIG. 3.

The data binning method 50 begins with the recognition of the provided test data set (block 52). In other words, the test data files are read into memory and recognized as being provided by the data binning algorithm 50. Thereafter, all single parameter histograms for each parameter are generated from the raw data of the test data set and optionally smoothed.

Generation of such histograms and smoothing thereof are generally known in the art. Double-precision, floating-point numbers (e.g., integer or non-integer values) are based on the relative sizes of the test data set. The total number of events (e.g., cells) in each file are, by default, normalized, but this can be overwritten to allow for normalization over sub-regions of the data set.

This ability to normalize over sub-regions of the data set provides an additional embodiment of the present invention. For example, a user (e.g., researcher) may employ subtractive clustering according to the present invention in a supervised mode or an unsupervised mode. In the unsupervised mode, the normalization, for example, may be defaulted (as well as various other settings) to a similar number of total cells. Frequently, subtractive clustering may be performed in the unsupervised mode to get a general feel for the data. Thereafter, if necessary, for example, the subtractive clustering algorithms may be run in a more supervised mode to explore the data sets in more detail, explore portions in more detail, or for any other reason. In the supervised mode, various controls may be set by a user. For example, with reference to FIG. 7, a certain number of parameters may be selected or ignored in section 330; various bin boundaries may be defined or adjusted in sections 336, 338; file weights may be set per sections 309, 310; etc.

Data points (i.e., coordinates) are generated from the test data set (block 54). In other words, for example, as used below to illustrate binning, consider a three-dimensional data set, with the three parameters plotted on x, y, z axes in a multi-dimensional space. A data point may be an event, e.g., a cell, with measurements x, y, z, equal to 100, 50, 200. Data points for all the events (e.g., cells) are generated.

The test data set is then grouped by processing or considering the generated data points and placing them into one or more bins (block 56). Preferably, the data points are sequentially considered. In general, the binning method 50 subdivides the original listmode test data into subgroups in multi-dimensional space, but not on the basis of either calculating multi-dimensional distances or reassigning data points to different clusters on the basis of a computationally intensive minimization algorithm as is done by conventional cluster analyses. Instead, the data binning method 50 estimates densities of data points in multi-dimensional data space on the basis of some simple algorithms performed on some or all of the histograms of the data. In other words, some or all of the measured parameters for the test data are considered. The ability to ignore some parameters is possible. For example, some parameters may be unhelpful or even confuse the optimal classification of data. Additionally, an ignored parameter, excluded from the subtractive clustering algorithms, can be used as a truth set to help determine the accuracy and usefulness of the subtractive clustering process.

Such grouping or binning of the generated data points can be described as calculating multi-dimensional "moxels"

Figure 4:
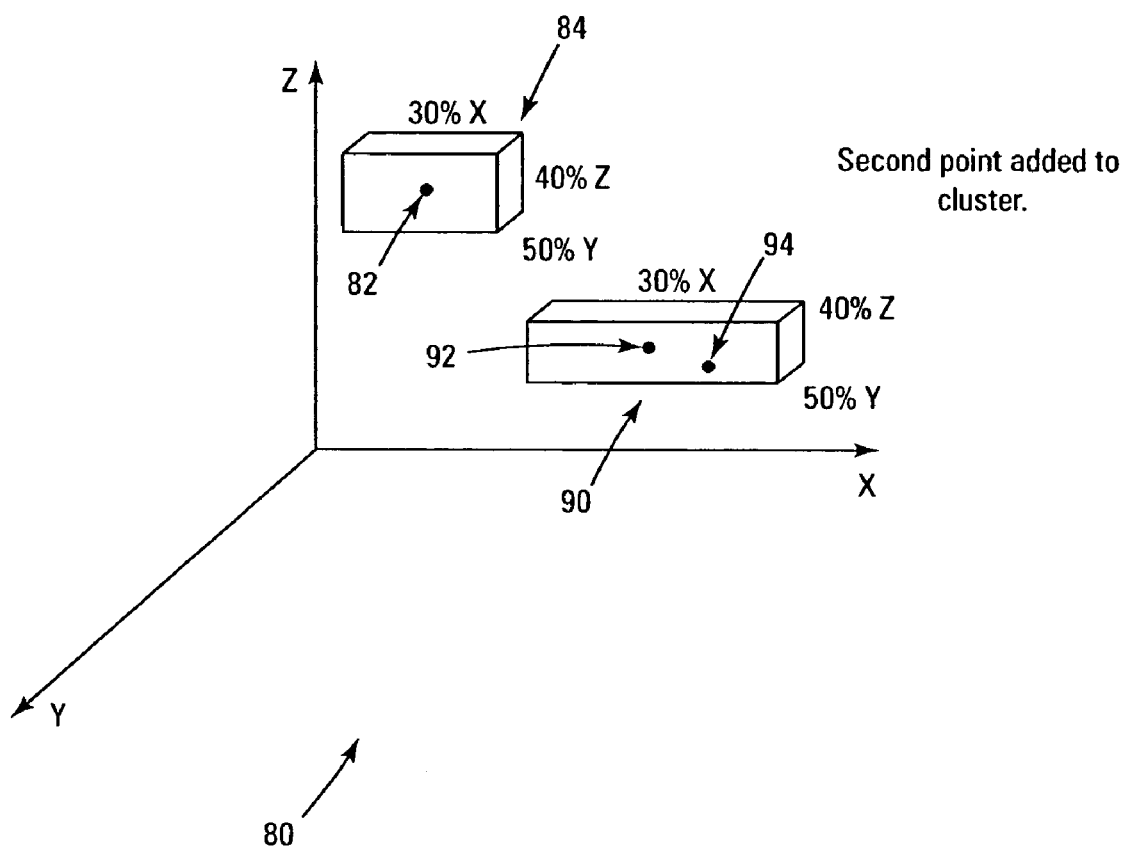
FIG. 4 shows an illustrative multi-dimensional space including defined clusters for use in describing the data binning method of FIG. 3.

(e.g., multi-dimensional boxes when considering three parameter events) in the multi-dimensional data space, for example, as shown in FIG. 4. The data binning method 50 uses variably-sized multi-dimensional moxels to classify the cells. The data bin boundaries for each parameter can be separately set allowing use of mixed data types. In other words, for example, a given parameter may be categorical rather than digitized intensity. Any type of parameter is envisioned according to the present invention, e.g., digitized values, text, etc.

Since computationally intensive distance minimization techniques are not used, large numbers of cells can be rapidly classified. This method allows rapid grouping of cells in sparsely populated multi-dimensional regions at full 12-bit (4,096 channel) resolution. It also allows the researcher to ignore fine resolution in the measurement process that may not be physically or biologically meaningful.

The sequential consideration of the data points and placement of the data points in one or more bins (block 56) (e.g., moxels) shall be described more specifically with reference to the illustrative three dimensional space 80 shown in FIG. 4. The binning is initiated by reading in a first data point 82 which automatically creates a bin 84 as shown in FIG. 4. When this first bin 84 is created, the first data point 82 is prescribed as the initial and center point 82 of the bin 84.

A set of bin boundaries for the first bin 84 are then resolved for each parameter of the data points being considered (block 60). In other words, for example, a set of fixed high and low rectilinear boundaries are resolved for each parameter of the data being considered when three parameters of the data are being analyzed.

For example, consider the three-dimensional data set previously mentioned, where three parameters are plotted on x, y, z axes in the multi-dimensional space 80 for a first data point 82 (e.g., a cell with measurements x, y, z, equal to 100, 50, 200). This first data point is made the center point 82 of the three-dimensional bin 84 as described above. The bin boundaries can then be set, for example, as 100+/−ax, 50+/−by, 200+/−cz. The bin 84 thus produced may also be referred to as a multi-dimensional box or a MuDbox. For example, assuming that ax=by=cz=1, then bin 84 is set up to cover x=99 to 101, y=49 to 51, z=199 to 201.

After the first data point 82 is set as the center point of the initial first bin 84, the next sequential data point in the test data set either fits into the bin 84 or will not fit into the bin 84. For example, consider a data point 92 as shown in FIG. 4 (i.e., data point 92 having x,y,z measurements of 105, 51, 199). This data point 92 does not fit into bin 84 due to its x-value. As such, a second bin 90 is set up with the second data point 92 as its center. Once again, bin boundaries are set up for bin 90 (block 60). Therefore, bins 84, 90 are created as each event (i.e., data point or set of cell measurements) is read in from the test file data set.

If the second data point 92 was such that it did fit into bin 84 (e.g., a point having values 99.7, 50.2, 199.3), then it would have been listed in the bin 84 (this is not shown in FIG. 4) as an additional coordinate. If the second data point 92 not only fit into bin 84 but had the same x, y, z set of values (e.g., 100, 50, 200) as first data point 84, then it is listed into the bin 84 and that particular like coordinate is incremented by a user-defined weighting value.

Once multiple bins (e.g., bins 84, 90) have been set up, when a subsequent event or data point is read in and considered, it is determined which bin is the nearest existing bin to which the subsequent data point may belong, if any. In consideration of such subsequent events, the user may select between Euclidean and Manhattan distance calculations to determine the minimum distance between the subsequent event or data point being read in and all the existing bins (e.g., bins 84, 90). As one would recognize, other metrics may be used.

In other words, the distance calculations are determined between the subsequent data point being read in and the center points of each of all the existing bins. The bin whose center point is closest, is considered the minimally distant bin.

It must then be determined whether the subsequent data point or event being considered belongs in the minimally distant bin, and as such whether it should be added to the minimally distant bin. For example, if the data point not only fits within the minimally distant bin, but also has the same coordinates as a data point therein, then the corresponding data point (i.e., coordinate) is incremented by a user-defined weighting value. If the event belongs in the minimally distant bin, but does not have the same coordinates as a data point already therein, then the data point being considered is merely added to the bin. If the data point being considered does not fit within the minimally distant bin, then a new bin is created with that event (i.e., the data point being considered) as its center point.

As shown in FIG. 4, a third sequential data point 94 has been considered. As this data point 94 fits within bin 90 but does not have the same coordinates as any of the other data points therein, the third data point 94 is added as a new coordinate to the bin list for bin 90.

The consideration of data points and placement in one or more bins continues until all desired data points have been considered (block 62). A bin containing more than one data point (e.g., bin 90) is considered a group (i.e., cluster) (block 64).

The binned data is stored as lists of clusters with associated center points and the other data points within the clusters. Each cluster has a file weight assigned to it, representing the number of data points that are within the cluster.

The bin boundaries for the bins may be determined in a variety of manners. For example, in one embodiment, the user may select between two methods and supply a factor for the method selected. For example, the user may select a method that uses a fixed percentage of the total number of counts in the test data set for the entire range of a given parameter. For example, if the x axis is the fluorescence intensity for a probe-1 and the x values of 80 to 250 are present in the list, then one might set a boundary of 1% of that range or +/−1.7. If the y axis represents the florescence intensity for probe-2 and y values of 40 to 90 are present in the list, one may use a bin boundary of 1% of the range or +/−0.5.

Another method of setting the bin boundaries, for example, may use a user-supplied multiplier for the regionalized fraction of the population within a particular area of interest for each parameter. For example, if the user is only interested in the area of interest containing x values of 100 to 120, despite the fact that x values of 80 to 250 are present in the test data set, and has supplied a multiplier of 0.02, then the x-boundary is x+/−0.02x.

Essentially, the data binning method 50 is an algorithm for rapid determination of the regions of higher population density in multi-dimensional space. After all the test data points have been considered and binned, and groups having a plurality of data points therein have been identified, such groups of clustered data points are provided for comparison (block 66). For example, subtraction data points (e.g., control data points) may be subtracted therefrom.

Normalization is used as a tool in subtractive clustering according to the present invention with a three-fold purpose. First, normalization provides a common factor to data from both test and control data sets among unchanging cell subpopulations. Second, normalization pulls out the specific "populations of interest" no matter what parameter is being considered. Third, normalization makes the subtractive clustering independent of human pattern recognition, while at the same time allowing the user to provide necessary input based on the knowledge of the researcher about the cell sample being analyzed.

For example, the user is allowed to set normalization weighting values. If the number of events in the data files is equal, then the weights for those files are equal. Otherwise, the number of events in two files can be forced to be equal by a global normalization process. Alternatively, the normalization factor can be set to any desired level to permit comparisons between subsets with two or more data sets (e.g., sub-region normalizations).

One issue that needs consideration is how to process weighting factors of a fractional cell number. This becomes an issue when the data points of a region are sparse. To solve this issue, a threshold percentage value is generated for each fractional cell number (referred to as "cell count") and then used to compare with whole cell values per each parameter. For binning of several fractional cell numbers (e.g., in a three parameter comparison), the high and low rectilinear boundaries are determined as previously described, e.g., multi-dimensional box percentages are set. Next, the new resultant cell count is added to the bin list. If the "multi-dimensional box percentage" is satisfied, the high and low bounds are then set. If the percentage value has not been satisfied, then the channel value weighted as 1 is then added to the bin list and tested for having attained the "MUD box percentage." If the percentage is now satisfied, the bounds are set for this parameter and, if not, then an offset of two channels is used above and below the first cell count so as to add to the total number of counts within the region. If this process is still unsuccessful, the offset is incremented and the operation continued, resulting in an ever-widening area centered on the initial channel of the single parameter projection, until the multi-dimensional box percentage is finally achieved. Once the upper and lower bounds of the parameter range is reached, the channel numbers are no longer added. When the bounds have been set for this fractional cell bin/cluster, the coordinate generated is added to the bin list, and the file weight is assigned and mapped to the coordinate in the data space as described earlier.

Like the test data set, the data of the control data set (i.e., the subtraction data set provided per block 18) is also read into memory. All single parameter histograms for the control data set are generated from the raw data and optionally smoothed. Double-precision, floating-point numbers (e.g., integer or non-integer values) are based on the relative size of the control data set. The total number of events in the control data set are usually, by default, normalized, but again this can be overwritten to allow for normalization over sub-regions of the data.

Figure 5:
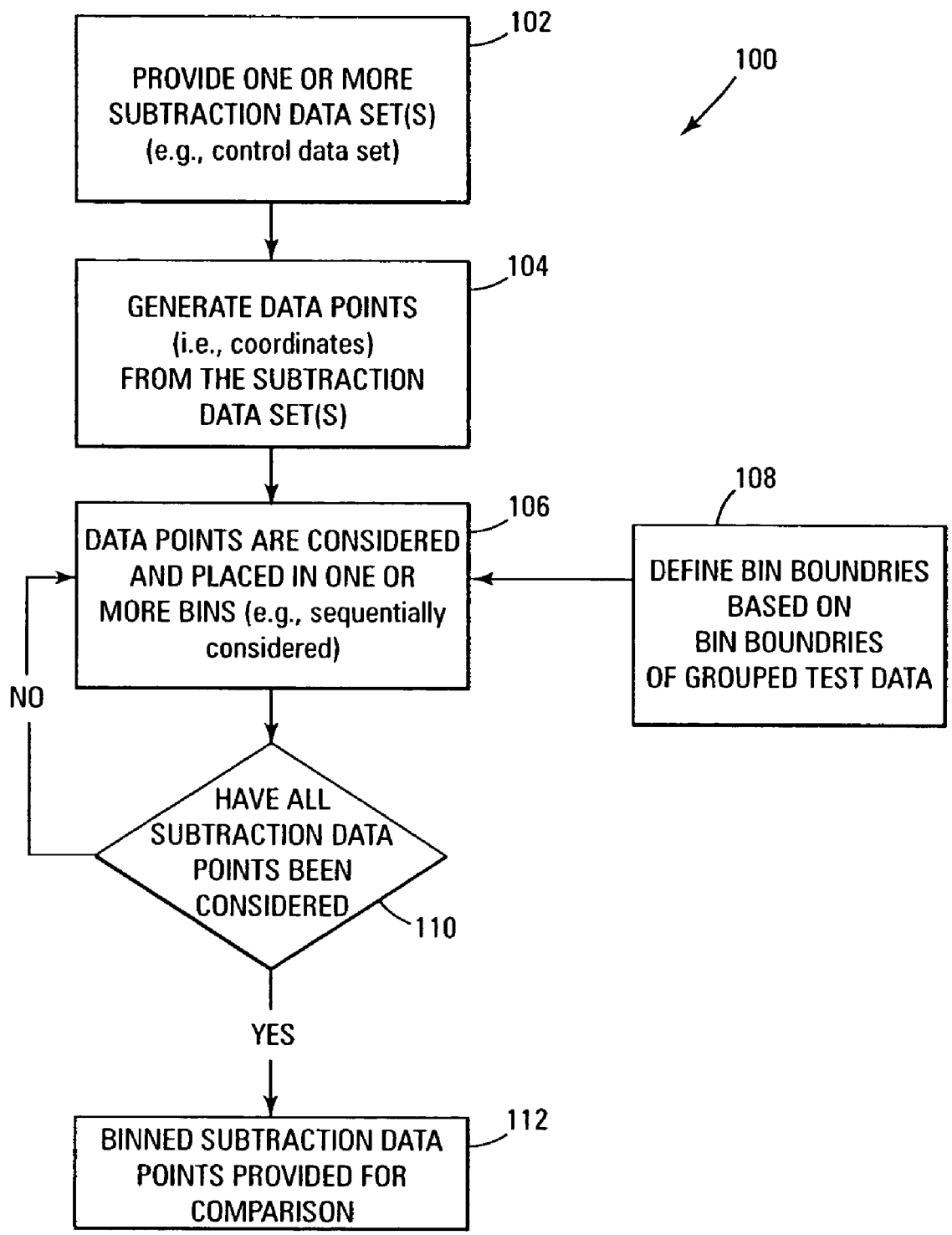
FIG. 5 is a flow diagram of an illustrative binning process for binning subtractive data points for use in the subtractive clustering method generally illustrated in FIG. 2.

The control data set is preferably binned prior to subtraction of data points from the test data set. One illustrative subtraction data binning method 100 is shown in FIG. 5. Like the test data set, control data points (i.e., control coordinates) are generated (block 104) from the control data set (block 102). In other words, for example, as used above to illustrate binning, consider a three-dimensional data set, with the three parameters plotted on x, y, z axes in a multi-dimensional space. A control data point may be an event, e.g., a cell, with measurements x, y, z, equal to 100, 50, 200. Control data points for all the events (e.g., cells) are generated.

Each of the subtraction data points, e.g., control data points, are considered and placed into one or more bins (block 106). The bins for the control data points are defined by the bin boundaries of the groups used to group the test data (block 108). In other words, if the subtraction (i.e., control) data point being considered falls within a defined bin (i.e., a bin defined by the bin boundaries of one of the groups of test data points), then the control data point being considered is placed in a bin defined by such bin boundaries. Just like when binning test data, if another like data point is already in the bin, then the weight of the coordinate of the data point is increased by a weight value.

If the subtraction (i.e., control) data point being considered does not fall within a defined bin (i.e., a bin defined by the bin boundaries of one of the groups of test data points), then the control data point being considered is discarded (not shown on FIG. 5). When all the control data points have been considered and binned (block 110) then the binned control data points (e.g., weighted binned subtraction data points) are provided for comparison to the clustered test data points. For example, the control data points may be subtracted from the clustered test data points.

With one or more groups of test data points provided (e.g., per block 66) along with one or more groups (i.e., bins) of subtraction data points (e.g., grouped control data points per block 112), the grouped control data points are then subtracted from the groups (i.e., clusters) of test data points (block 24) as shown in FIG. 2. One illustrative embodiment of data subtraction block 24 as shown generally in FIG. 2 is illustrated by data subtraction method 150 of FIG. 6.

Figure 6:
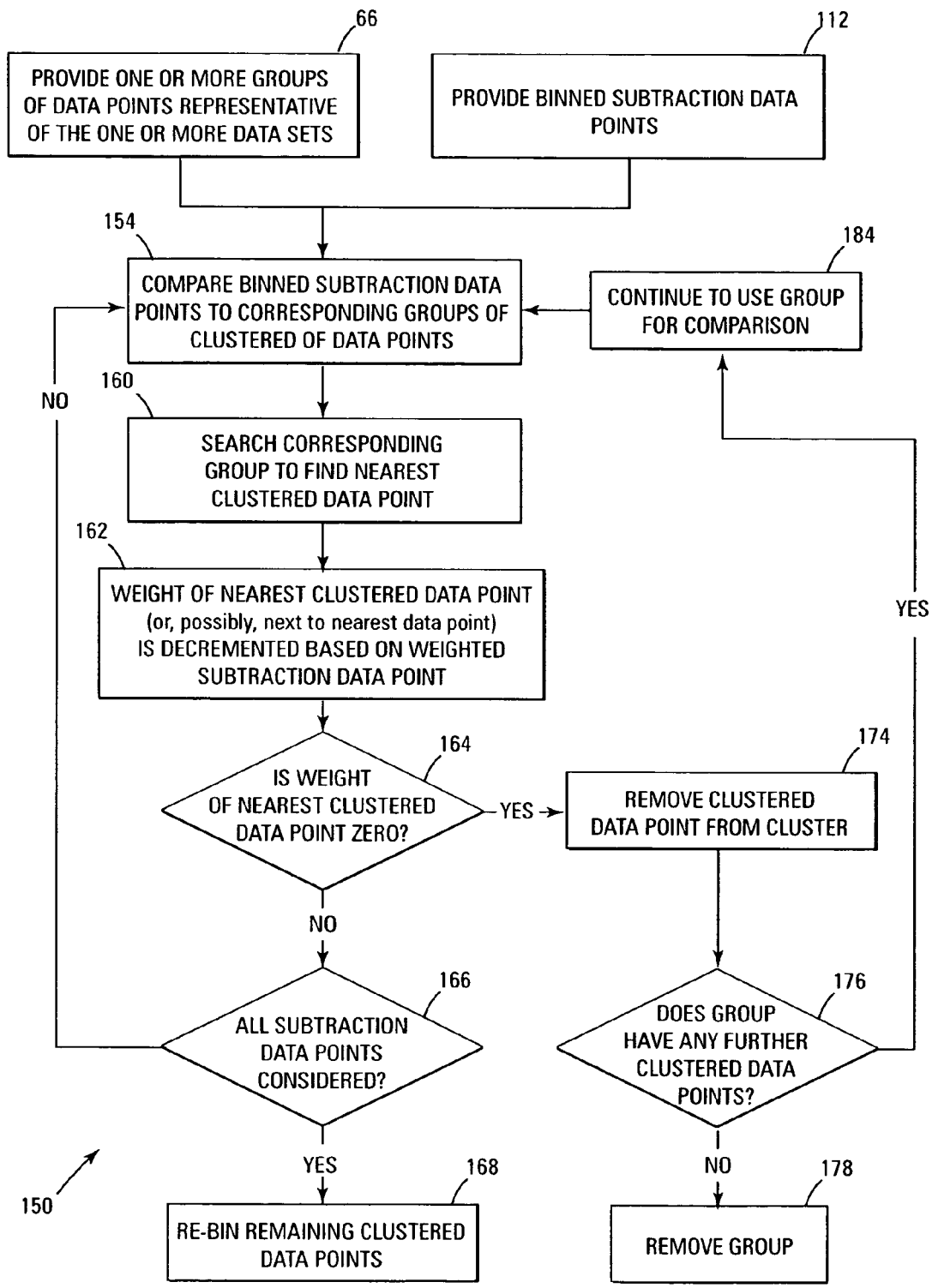
FIG. 6 is an illustrative flow diagram of a data subtraction method for use in the subtractive clustering method shown generally in FIG. 2.

As shown in FIG. 6, the data subtraction method 150 includes comparing the binned subtraction data points to the one or more groups of weighted clustered test data points (block 154). For each subtraction data point of a particular bin having defined bin boundaries (i.e., bin boundaries corresponding to the bin boundaries of the groups of test data points), the group of test data points having the corresponding bin boundaries is located; this group may be referred to as the nearest cluster (i.e., corresponding group) of test data points for the subtraction data point being considered.

Since the binned subtraction (i.e., control) data point falls within the defined boundaries of the corresponding group, then the test data list (i.e., clustered test data points) associated with the corresponding test group (i.e., nearest cluster) is searched to find the clustered test coordinate (i.e., data point) nearest to the control data point being considered (block 160). Once the nearest clustered test data point is found, the weight of the nearest clustered test data point is decremented based on the weight of the subtraction data point (block 162). In other words, the weight of the nearest coordinate or data point in the nearest cluster (i.e., corresponding group having like bin boundaries) is decremented by the control file weight associated with the subtraction (i.e., control) data point being considered.

If a test data point or a coordinate's weight is finite but not sufficient to allow subtraction of the weight of the subtraction or control data point, the process proceeds with a subtraction from the next closest test data point in the cluster list. Such a search and subtraction from the next closest test data points continues as long as there is weight left in the control data point to be subtracted.

If the weight of the nearest clustered data point is 0 after subtraction of the control (i.e., subtraction) data point (block 164), it is removed from the group (i.e., cluster) (block 174). Thereafter, it is considered whether that particular group has any further clustered data points (block 176). If other clustered data points are available, then the process is continued by using the group where the subtraction occurred for further comparisons to other control data points that fall within bins defined by the corresponding bin boundaries of the group (block 184). However, if the group (i.e., cluster) does not have any further clustered data points, then the group is removed (block 178).

After subtraction of the subtraction data point (i.e., control data point) from the nearest data point is performed, and further if the weight of the nearest clustered data point is not 0 (block 164), then it is determined whether all subtraction data points have been considered (block 166). If all the subtraction data points have not been considered, then further comparisons are made between subsequent subtraction data points and the one or more corresponding groups of clustered data points (block 154).

Upon subtraction of all subtraction data points from the clusters of clustered data points, then data reconstitution or re-binning (block 168) is performed. In other words, the subtracted or difference list file of clusters is reprocessed coordinate-by-coordinate (i.e., data point by data point) into a new subset of data.

For example, the resulting difference, i.e., the difference data points resulting from the subtraction of the control data points from the test data points, are re-binned. The number of data points per coordinate is determined by subtracting a user set threshold value from the coordinate and dividing the result by a user defined event step value or weight value. In other words, the same weight value used to increment the weight of like data points in the clustering process may be used to determine the number of events per data point or coordinate in the re-binning process. The subtracted data file or difference data file can then be written out in a desired format.

One will recognize that once corresponding groups of two multi-dimensional data sets have been generated (i.e., such groups having corresponding bin boundary definitions so as to indicate their similarity), then any process of subtracting the data points of one set from the other on a group to corresponding group basis is contemplated according to the present invention. For example, a nearest cluster averaged subtraction process may be used. In one illustrative alternate nearest cluster averaged subtraction process, each subtraction data point (i.e., control data point) may be subtracted from an averaged value of test data points taken over a fractional region of the group of test data points.

Figure 7:
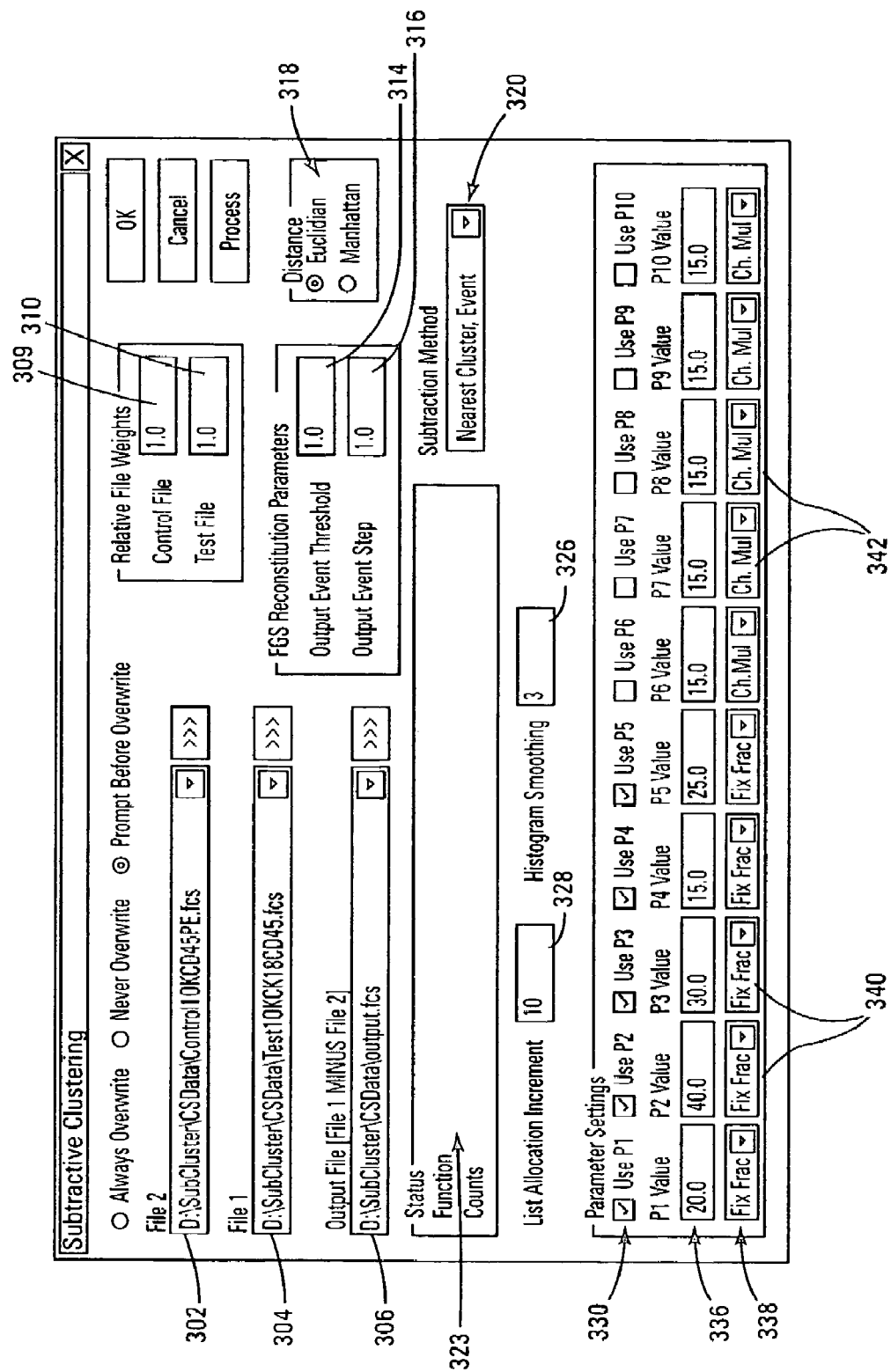
FIG. 7 shows an implementation of a user interface for allowing a user to define one or more parameters for the subtractive clustering method shown generally in FIG. 2.

The data processing system 14 executing the data mining algorithm or subtractive clustering method 20 is operable under control of a user by way of a user interface for allowing individual parameter adjustment of the process. One illustrative user interface for the subtractive clustering software 20 is shown in FIG. 7. As shown therein, the user interface 300 allows the user to select the files to be compared as shown by pull-down block 302 and pull-down block 304. The output of this subtractive clustering process is provided and can be selected by pull-down menu 306.

The user is allowed to select the relative file weights for both the control data set and the test data set as shown by entry blocks 309, 310, respectively. Further, the user may choose either Euclidean or Manhattan distance calculations per selection block 318 to determine which distance method is used for finding the nearest cluster when binning data as described herein with reference to FIGS. 3 and 4. The entry blocks 314 and 316 provide the user the ability to enter output event thresholds and output event steps for reconstitution of the data after the subtractive step is completed. Pull-down menu 320 allows the user to select a particular subtraction method, e.g., nearest cluster event subtraction method or nearest cluster average subtraction method, as described previously herein with reference to FIG. 6.

The list allocation increment entry block 328 provides the user with the ability to set the resolution of the data. Further, the histogram smoothing entry block 326 provides the user with the ability to enter a user-defined smoothing kernel created for each parameter.

Yet further, the user interface 300 provides for allowing the user to define parameter settings, e.g., select which parameters are to be used or ignored as shown in region 330. Further, the parameter settings region 336 and 338 allows for the user to define criteria for setting bin boundaries as previously described with reference to FIGS. 3 and 4 herein. As such, the user is given the ability to control either on an individual parameter basis by using a fixed percentage process 340, or by some user-defined multiplier 342. Providing for individual parameter definition allows use of mixed type data as previously discussed herein.

Further, a status section 323 provides for indication of the status of the subtractive clustering algorithm according to the present invention as it is running.

Subtractive clustering according to the present invention may be used in a variety of applications as previously described herein. For example, subtractive clustering can be used to find the differences between test and control multi-parameter flow cytometric data, e.g., in a problem of human stem cell isolation with tumor purging. Further, subtractive clustering can provide training data for subsequent multivariate statistical classification techniques such as DFA or LRA. In addition, as is known, using look-up tables, multivariate statistical calculations can be performed in real-time, and can even include probabilities of misclassification.

Figure 8:
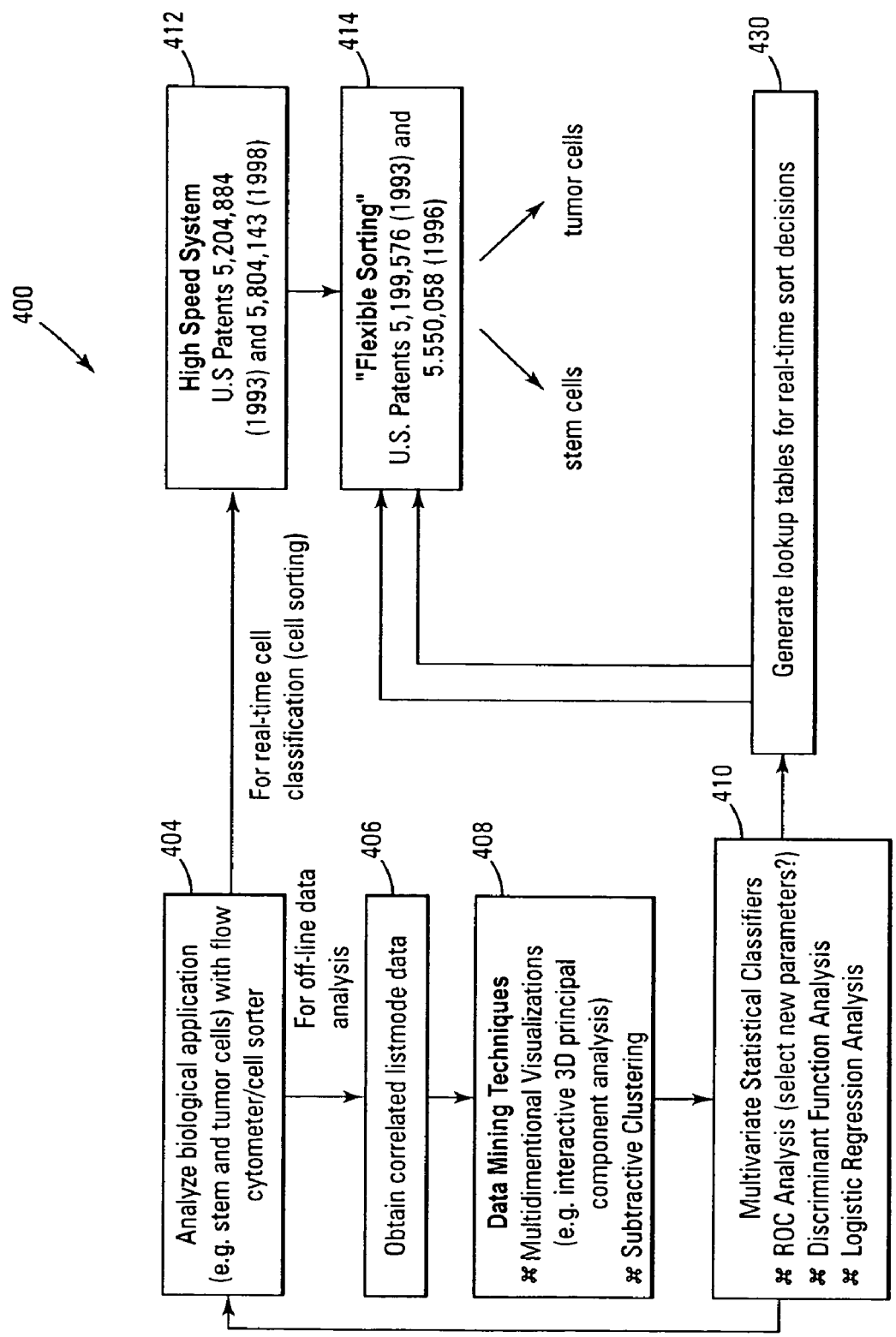
FIG. 8 is a block diagram of an illustrative flow cytometry/cell sorting process using subtractive clustering as a data mining method to assist in establishing sort decision boundaries according to the present invention.

FIG. 8 shows a block diagram of a flow cytometry/cell sorting process 400 which uses subtractive clustering as described herein. As shown in FIG. 8, a biological application sample (e.g., stem cells and tumor cells) is analyzed using flow cytometer/cell sorter (block 404). The biological sample is provided through a flow cytometer for obtaining correlated listmode flow cytometric data representative of the biological sample (block 406). Such flow cytometry is well-known in the art and shall not be described in any detail herein.

Various data mining techniques may then be utilized with respect to the flow cytometric data (block 408). For example, an experimenter may use multi-dimensional visualizations to identify cell subpopulations of interest. Such multi-dimensional visualizations may include interactive 3-D PCA. Further, for example, various histograms and bivariate displays may be obtained. The experimenter may then use human pattern recognition to identify cell subpopulations of interest.

Further, according to the present invention, subtractive clustering may be used for data analysis as previously described. For example, a control data set of stem cells may be subtracted from the flow cytometric data of stem and tumor cells. The resulting data set may then be used by the multivariate statistical classifiers as shown in block 410.

The multivariate statistical classifiers 410 may be used to generate look-up tables for setting gates used as sort decision boundaries in real time sorting processes. Various multivariate statistical classifiers may be used for the multi-dimensional data described herein. For example, such multivariate statistical classifiers may include ROC analysis, DFA, and LRA. One skilled in the art will recognize that any multivariate statistical classifier may be used according to the present invention and the present invention is not limited to any particular multivariate statistical classifier technique.

The subtractive clustering method according to the present invention may be used in conjunction with flow cytometric data for various purposes. For example, subtractive clustering can be used once, or multiple times, to generate relatively pure training sets of each group (or cell subpopulation) for subsequent analysis by DFA or LRA. Quite commonly, one is unable to obtain purified cell subpopulations or groups experimentally. Only cell mixtures are available for analysis, so the training groups must be extracted from this data. The process of subtractive clustering yields separate data files for each group which can then be input as training groups to one or more various statistical packages such as SAS™ or S-Plus™ (available from MathSoft, Inc., Seattle Wash.) for subsequent DFA or LRA.

As indicated above, the multivariate statistical classifiers are used to set gates for making sort decisions in real-time using look-up tables linked to sort decision hardware. The actual classification can be one step for conventional applications or a high speed, two-step classification procedure for rare event analyses requiring very high rates of cells per second. Various systems have been described in the art. For example, high-speed systems 412 have been described in U.S. Pat. No. 5,204,884 entitled, "System for High-Speed Measurement and Sorting of Particles" issued Apr. 20, 1993, and U.S. Pat. No. 5,804,143 entitled, "System for High-Speed Measurement and Sorting of Particles" issued 8 Sep. 1998.

Yet further, flexible sorting 414 wherein sort decisions can be generated from mathematical algorithms combining information from multiple sources have also been described, such as in U.S. Pat. No. 5,199,576 entitled, "System for Flexibly Sorting Particles, issued 6 Apr. 1993, and U.S. Pat. No. 5,550,058 entitled, "System for Flexibly Sorting Particles, issued 27 Aug. 1996. Subtractive clustering could be used as a possible source of information to use with either conventional sort boundaries or more sophisticated algorithmically-driven flexible sorting methods.

Figure 9:
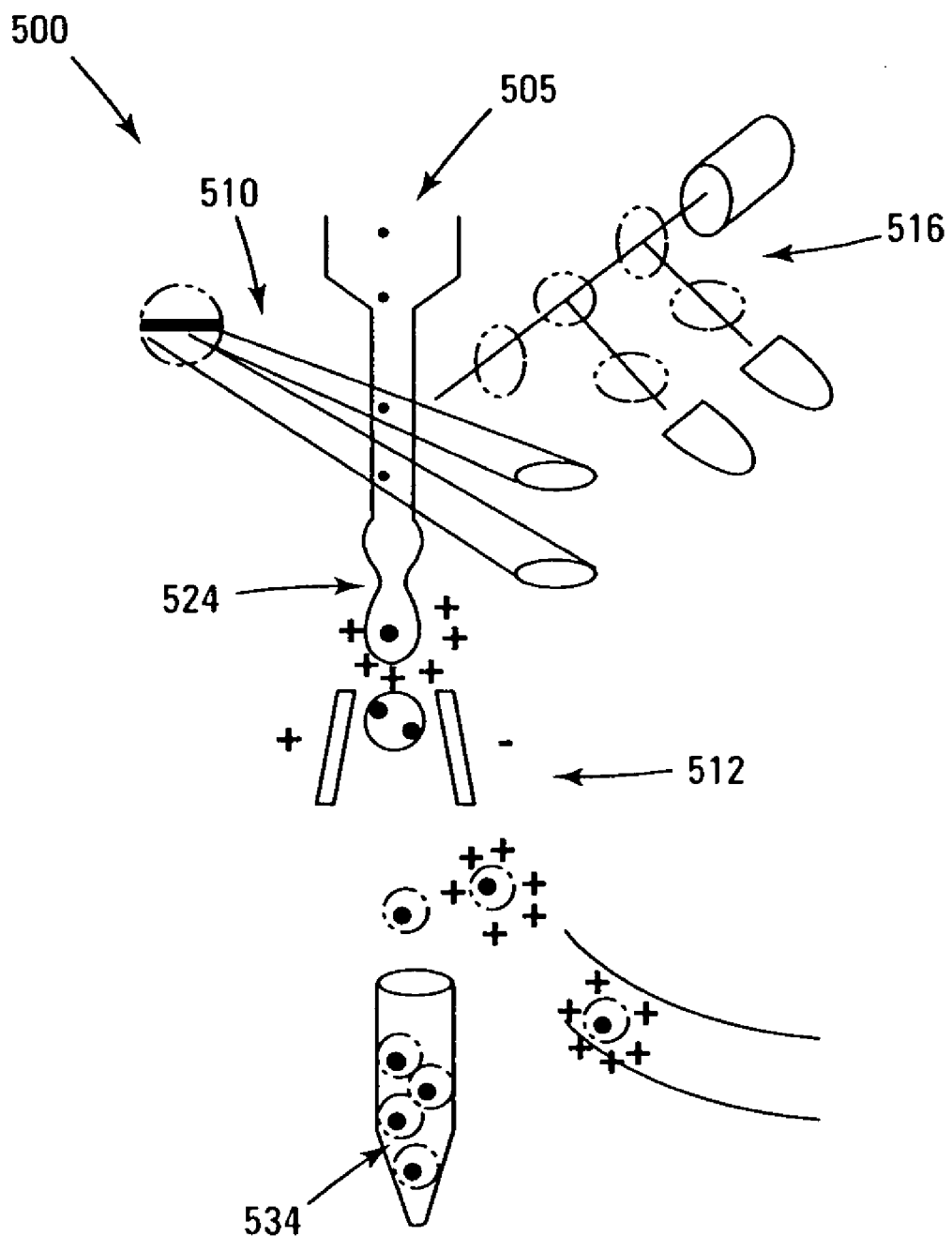
FIG. 9 is a generalized flow cytometry/cell sorting apparatus which may use subtractive clustering according to the present invention to make sort decisions.

Generally, for example, the systems for sorting minute particles in a fluid may be referred to as a cell sorting apparatus or system. For example, such systems may use optical measurements of characteristics of each particle of a group of particles made while the particles are suspended in a sample to provide sorting information. In one such system 500, at least partly shown in FIG. 9, a cell sorter analyzes cells or particles in suspension 505 which are labeled with a fluorescent marker and are carried single file in a fast moving liquid stream sequentially through at least one tightly-focused laser beam 510 whose wavelength is adjusted to illuminate the fluorescent dye. The fluorescent produced during the laser beam crossing is collected by an optical system 516 projected through special filters onto photo detectors. These detectors convert the fluorescent to electrical pulses whose amplitudes depend on total light reaching the detectors. Particles having predetermined characteristics are recognized by their distinctive fluorescence.

After measurements of the characteristics, each particle flows in a liquid jet stream until the particle reaches a point 524 where the jet breaks into discrete droplets. At this point, an electrical charge is induced on each droplet containing particle to be sorted, and the charged and uncharged droplets are then sorted electrostatically into appropriate recovery vessels, e.g., using deflection plates 512. In such a manner, sorted droplets 534 containing cells of interest can be obtained. A variety of other non-droplet sorting devices still require real-time sort decisions to be made on the basis of incoming two or more dimensional data.

One skilled in the art will recognize that various configurations of flow cytometers or cell sorters may be utilized in accordance with the present invention and benefit from the advantages provided by subtractive clustering. As such, the present invention is not limited to any particular flow cytometer/cell sorter.

In summary, the present invention includes various features and can be employed in a variety of different manners. For example, one feature of the present invention is that data points need only be similar (e.g., as defined by a user), not numerically identical, to be compared. Another feature is the manner in which the present invention can look at the similarities and differences between two or more data sets. Other clustering algorithms typically look only at the data subgroups or clusters within one data set. The data resulting from the comparison of two or more data sets (e.g., subtraction) can be re-binned so that it (e.g., a subset of the original data) can be re-analyzed or displayed (e.g., using the same software as used for the original data).

Further, at least in one embodiment, the present invention does not require clustering on the basis of relative density of points in a given cluster. Therefore, clusters can contain amorphous data groupings without well-defined peaks (e.g., which are typically a requirement of many conventional clustering algorithms) or data groupings of very sparsely distributed data points, as is the case for small numbers of data events in higher dimensional data spaces.

Another illustrative feature of the present invention is the ability to group data that is categorical or non-numerical. Hence, it can be readily applied to mixed data types.

Further, the present invention has the ability to analyze data with different scaling factors for each measured parameter, as is the case for most flow or image cytometry data sets. This allows for re-analysis of subsets of the original data (e.g. the re-staining and/or re-analysis by flow or image cytometry of the original cells, or by the molecular characterization of physically sorted cell subpopulations by PCR, gene-expression or protein-expression microarray analysis, etc.

As described herein, subtractive clustering according to the present can be performed in either an unsupervised or a supervised mode. Typically as a data discovery/mining method it is first performed in a totally unsupervised mode. As more is known about the data, sub-regions of the data sets can be normalized with respect to each other in a more supervised mode (e.g., sub-region normalization) to extract more information about the similarities and differences between data sets.

As mentioned on numerous occasions, the present invention may be applied to more than two multi-dimensional data sets. As such, it may be used in situations where one must look at more than one control data set or even controls within controls. In other words, for example, subtractive clustering according to the present invention may be performed iteratively to compare more than two data sets (e.g., two control sets and a test set) or subtractive clustering analysis may be applied to three or more data sets non-iteratively.

Since the subtractive clustering methods described herein are not computationally intensive, very large data sets can be compared on non-high end computers. This is not possible using most conventional cluster analysis algorithms. Further, since the methods do not require storage in memory (e.g., disk) of large, multi-dimensional arrays, the process does not become computationally difficult as the number of data dimensions increases, nor does the bit resolution of the data need to be reduced in order to reduce computational demands.

The user interface of the present invention provides a user with various controls. For example, one or more parameters of the multi-dimensional data set can be ignored to either improve distinction between subsets of the data or the excluded parameters can be used as a truth set for algorithm testing.

The results of subtractive clustering can be implemented for a number of different purposes. For example, the results may be employed to provide a lookup table or as an embedded algorithm to provide for real-time classification of incoming data streams or to provide for real-time sorting of physical objects corresponding to this data stream.

Yet further, the present invention is useful for extracting "rare" data objects, where the limits of this rare-event condition are limited only by the ability of a number of correlated variables to distinguish one rare event from another in a meaningful way. In other words, it can deal with sparse data in high-dimensional data spaces.

Lastly, it is recognized that subtractive clustering as described herein is general in terms of types of data that can be analyzed, but is especially applicable to flow and image cytometry data, multi-spectral imaging data, and gene-expression and/or protein-expression microarray data.

To illustrate the results of the present invention, the following example is provided.

EXAMPLE

This example applies the subtractive clustering program with its outputs coupled with Boolean logic gating within the listmode processor program WinList™ 4.0 for Microsoft Windows 95/NT™ (Verity Software House, Inc., Topsham, Me.). The results of this simple but instructive illustration of the present invention are shown in FIG. 10.

The optics of the flow cytometry system were deliberately de-optimized to insure flow cytometric overlap of two bead types (i.e., FITC beads and Nile Red beads) while allowing for easy detection of sorted beads of each type by a human observer using fluorescence microscopy to directly visualize sorted beads to provide a truth set for determining how well the subtractive clustering allowed setting of multi-dimensional sort gates.

In this illustrative example, an attempt was made to isolate two subpopulations of microspheres from a mixture of the beads, so as to provide two training sets for applying DFA to real flow cytometry data for data analysis and sort boundaries based on the statistical decision theory. For this example, commercially available standardized microbeads were employed. A training set, or File 2, was obtained from a raw FCS data file using Quantum™ 25 microbeads, 825-4b (FCSC, San Juan, PR, USA), which are fluorescently labeled with FITC. A mixture, or File 1, was achieved by making a dilution of the FITC beads with another set of beads, called SPHERO™ Fluorescent Particles, that are labeled with Nile Red (Spherotech, Libertyville, Ill.). The cells were analyzed on a high-resolution cell sorter system, using a 5W water-cooled Spectra/Physics Model 2025 argon-ion laser tuned to 488 nm at 500 mW. Each FCS file had 10,000 events (i.e., beads).

The parameters selected via the user interface for the subtractive clustering process showed a set up for subtraction using the Euclidean distance metric, nearest cluster event, and channel multiplier with 4-parameter FCS data files. File 1 is the "test file data set," and File 2 is the "control file data set." The Output File is the difference between subtracting File 1 minus File 2 and is also in FCS 2.0 format. Relative file weights were user-defined and set to normalize the data over a particular region in the data space. Both the output event threshold and output event step were left at one.

The multiple subtraction process for this data was performed in two steps so that the Nile Red beads would stand out alone. The first step was to use subtractive clustering to remove the Nile Red data points from the mixed data by subtracting the Nile Red data from the mixed data (i.e., mixed minus Nile Red). Next, the FITC data was subtracted from the mixed data. By analyzing the bi- and trivariate displays for three of the four variables (data not shown), the cells were clearly divided into three populations: a large and a small FITC population, and the Nile Red population.

Panel A of FIG. 3 is the raw FCS data for both training set files for the two separate types of microbeads (i.e., FITC and Nile Red) with the distributions for each bead type (i.e., FITC distribution 600 and Nile Red distribution 602) overlaid on each other. Afterwards, the data was put through our discriminant function program to calculate the probabilities of misclassification.

Panel B of FIG. 3 is the subtractive cluster analysis based on the mixed bead sample, showing the FITC peak 620 as a result of the mixed data minus the Nile Red data, while the Nile Red peak 622 is shown as the result of the mixed data minus the FITC data. It should be noted that the forms of the projected distributions are almost identical, thus verifying the subtraction process, and serving to illustrate how precisely the subtractive clustering algorithm may pull out separate subpopulations from a mixture.

All references cited herein are incorporated in their entirety as if each were incorporated separately. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A computer implemented method for use in analyzing similarities or differences between two or more multi-dimensional data sets, the method comprising:
   providing two or more multi-dimensional data sets;
   providing a plurality of data points for at least a first multi-dimensional data set of the two or more multi-dimensional data sets, wherein each data point is representative of at least two parameters associated with an event of a plurality of events;
   grouping the plurality of data points into one or more multi-dimensional groups of clustered data points, wherein each of the one or more multi-dimensional groups is defined by one or more bin boundaries associated with the at least two parameters;
   providing a plurality of subtraction data points for at least a second multi-dimensional data set of the two or more multi-dimensional data sets, wherein each subtraction data point is representative of the at least two parameters associated with an event of a plurality of events;
   grouping the plurality of subtraction data points into one or more groups of subtraction data points based on the one or more bin boundaries of the one or more multi-dimensional groups of clustered data points, wherein each of the one or more groups of subtraction data points corresponds to one of the one or more multi-dimensional groups of clustered data points; and comparing the plurality of subtraction data points of one or more groups of subtraction data points to corresponding multi-dimensional groups of clustered data points resulting in data representative of similarities or differences between at least the first multi-dimensional data set and the second multi-dimensional data set.

2. The method of claim 1, wherein comparing the plurality of subtraction data points of one or more groups of subtraction data points to corresponding multi-dimensional groups of clustered data points comprises subtracting at least a plurality of the subtraction data points from similar, not necessarily identical, data points of the corresponding multi-dimensional groups of clustered data points.

3. The method of claim 2, wherein the clustered data points comprise weighted clustered data points, wherein the subtraction data points comprise weighted subtraction data points, and further wherein subtracting at least a plurality of the subtraction data points from similar, not necessarily identical, data points of the corresponding multi-dimensional groups of clustered data points comprises subtracting at least a plurality of the weighted subtraction data points from the corresponding multi-dimensional groups of weighted clustered data points.

4. The method of claim 3, wherein subtracting at least a plurality of the weighted subtraction data points from the corresponding multi-dimensional groups of weighted clustered data points comprises:

determining, for each weighted subtraction data point, the closest weighted clustered data point within a corresponding multi-dimensional group; and subtracting the weight of the subtraction data point from the closest weighted clustered data point.

5. The method of claim 4, wherein subtracting the weight of the subtraction data point from the closest weighted clustered data point comprises:

locating one or more next closest weighted clustered data points within the corresponding multi-dimensional group if the weight of the subtraction data point is in excess of the weight of the closest weighted clustered data point; and subtracting the excess weight from the one or more next closest weighted clustered data points.

6. The method of claim 1, wherein grouping the plurality of subtraction data points into one or more groups of subtraction data points comprises:

attempting to define, for each subtraction data point, a corresponding multi-dimensional group based on the one or more bin boundaries defined for the one or more multi-dimensional groups; and deleting a subtraction data point if it does not fall within a bin corresponding to one of the one or more multi-dimensional groups defined by one or more bin boundaries.

7. The method of claim 1, wherein comparing the plurality of subtraction data points of one or more groups of subtraction data points to corresponding multi-dimensional groups of clustered data points comprises subtracting at least a plurality of the subtraction data points from corresponding multi-dimensional groups of clustered data points resulting in difference data points, and further wherein the method comprises re-binning the difference data points so that they form a subset of the at least a first multi-dimensional data set.

8. The method of claim 1, wherein each data point is representative of a plurality of parameters associated with an event of a plurality of events, and further wherein the method comprises selecting, by a user, one or more of the plurality of parameters to be ignored when comparing the plurality of subtraction data points of one or more groups of subtraction data points to corresponding multi-dimensional groups of clustered data points.

9. The method of claim 1, wherein grouping the plurality of data points into one or more multi-dimensional groups of clustered data points comprises:

providing multiple bins, wherein each of the multiple bins has a data point of the plurality of data points recognized as a center point for the bin, and further wherein each bin is defined by one or more bin boundaries associated with the at least two parameters;

continuing to bin further data points of the plurality of data points, wherein continuing to bin further data points comprises:

evaluating, for each data point, the distance between the data point and the center points of defined multiple bins to identify the closest defined bin;

if the data point fits within the closest defined bin, then adding the data point to the closest defined bin; and if the data point does not fit within the closest defined bin, then recognizing the data point as a center point of another bin defined by one or more bin boundaries associated with the at least two parameters.

10. The method of claim 9, wherein the distance is calculated using a Euclidean distance calculation.

11. The method of claim 9, wherein the distance is calculated using a Manhattan distance calculation.

12. The method of claim 9, wherein providing multiple bins comprises:

recognizing a first data point of the plurality of data points as a center point of a first bin defined by one or more bin boundaries associated with the at least two parameters; and continuing to evaluate one or more other data points of the plurality of data points to determine whether the one or more other data points fit within the first bin, wherein continuing to evaluate other data points comprises:

if one of the one or more other data points fits within the first bin defined by the one or more bin boundaries, then adding the data point to the first bin resulting in a multi-dimensional data cluster of data points; and if one of the one or more other data points does not fit within the first bin, then recognizing the data point as a center point of a second bin defined by one or more boundaries associated with the at least two parameters.

13. The method of claim 9, wherein the method further comprises:

determining whether a data point has the same coordinates as a data point already in one of the multiple bins;

if the data point does not have the same coordinates, then adding the data point to the bin as an additional data point; and if the data point does have the same coordinates, then increasing the weight of the data point already in the one of the multiple bins.

14. The method of claim 1, wherein comparing the plurality of subtraction data points of one or more groups of subtraction data points to corresponding multi-dimensional groups of clustered data points comprises subtracting at least a plurality of the subtraction data points from similar, not necessarily identical, data points of the corresponding multi-dimensional groups of clustered data points resulting in a difference data subset, and further wherein the method comprises comparing grouped data of another multi-dimensional data set to the difference data subset.

15. The method of claim 1, wherein the method further comprises allowing a user to define at least one bin boundary associated with one of the at least two parameters.

16. The method of claim 15, wherein the method further comprises defining at least one bin boundary associated with one of the at least two parameters using a user-supplied multiplier for a fraction of a region of interest within the entire range for the parameter or using a fixed percentage factor relative to an entire range for the parameter.

17. The method of claim 1, wherein at least the first and second multi-dimensional data sets comprise data generated by analysis of gene expression or protein expression microarrays or other non-array processes.

18. The method of claim 1, wherein at least the first and second multi-dimensional data sets comprise data generated by at least one of flow cytometry analysis; imaging analysis; microarray analysis; and gel analysis.

19. The method of claim 18, wherein at least the first and second multi-dimensional data sets comprise data generated by multi-spectral imaging analysis.

20. The method of claim 18, wherein at least the first and second multi-dimensional data sets comprise data generated by flow cytometry analysis.

21. The method of claim 20, wherein comparing the plurality of subtraction data points to the one or more multi-dimensional groups of clustered data points to determine similarities or differences comprises identifying rare cell subpopulations in at least one multi-dimensional data set.

22. The method of claim 20, wherein comparing the plurality of subtraction data points to the one or more multi-dimensional groups of clustered data points to determine similarities or differences comprises identifying cell subpopulations in at least one multi-dimensional data set.

23. The method of claim 22, wherein the method further comprises using the identified cell subpopulations to set sort gates on a flow cytometer/cell sorter to isolate such cell subpopulations of a flow of cells provided therethrough.

24. The method of claim 22, wherein the method further comprises using the identified cell subpopulations as training sets for one or more subsequent multivariate statistical classifier processes.

25. The method of claim 24, wherein the one or more multivariate statistical classifiers comprise one of discriminant function analysis and logistical regression analysis.

26. The method of claim 24, wherein the method further comprises using results from the one or more multivariate statistical classifiers for use in look-up tables or for use in embedded algorithms, such look-up tables or embedded algorithms for use in making real-time sort decisions when running cell containing samples through a cell sorting apparatus.

27. The method of claim 1, wherein the one or more bin boundaries are individually definable for each of the at least two parameters, and further wherein at least the first and second multi-dimensional data sets comprise mixed data types.

28. A data mining system for use in analyzing similarities or differences between two or more multi-dimensional data sets wherein the system comprises a processing apparatus operable under control of a user interface, wherein the processing apparatus is operable to:

recognize a plurality of data points for at least a first multi-dimensional data set, wherein each data point is representative of at least two parameters associated with an event of a plurality of events;

group the plurality of data points into one or more multi-dimensional groups of clustered data points, wherein each of the multi-dimensional groups is defined by one or more bin boundaries associated with the at least two parameters and controllable by a user via the user interface;

recognize a plurality of subtraction data points for at least a second multi-dimensional data set, wherein each subtraction data point is representative of the at least two parameters associated with an event of a plurality of events;

group the plurality of subtraction data points into one or more groups of subtraction data points based on the one or more bin boundaries of the one or more multi-dimensional groups of clustered data points, wherein each of the one or more groups of subtraction data points corresponds to one of the one or more multi-dimensional groups of clustered data points; and compare the plurality of subtraction data points of one or more groups of subtraction data points to corresponding multi-dimensional groups of clustered data points resulting in data representative of similarities or differences between at least the first multi-dimensional data set and the second multi-dimensional data set.

29. The system of claim 28, wherein the processing apparatus is further operable to compare the plurality of subtraction data points of one or more groups of subtraction data points to corresponding multi-dimensional groups of clustered data points by subtracting at least a plurality of subtraction data points from similar, not necessarily identical, data points of the corresponding multi-dimensional groups of clustered data points.

30. The system of claim 29, wherein the clustered data points comprise weighted clustered data points, wherein the subtraction data points comprise weighted subtraction data points, and wherein the processing apparatus is further operable to subtract the plurality of subtraction data points from the corresponding multi-dimensional groups of clustered data points by subtracting at least a plurality of weighted subtraction data points from the corresponding multi-dimensional groups of weighted clustered data points.

31. The system of claim 30, wherein the processing apparatus is further operable to subtract the plurality of weighted subtraction data points from the corresponding multi-dimensional groups of weighted clustered data points by:

determining, for each weighted subtraction data point, the closest weighted clustered data point within a corresponding multi-dimensional group; and subtracting the weight of the subtraction data point from the closest weighted clustered data point.

32. The system of claim 31, wherein the processing apparatus is further operable to subtract the weight of the subtraction data point from the closest weighted clustered data point by:

locating one or more next closest weighted clustered data points within the corresponding multi-dimensional group if the weight of the subtraction data point is in excess of the weight of the closest weighted clustered data point; and subtracting the excess weight from the one or more next closest weighted clustered data points.

33. The system of claim 29, wherein the processing apparatus is further operable to group the plurality of subtraction data points into one or more groups of subtraction data points by;
attempting to define, for each subtraction data point, a corresponding multi-dimensional group based on the one or more bin boundaries defining the one or more multi-dimensional groups; and
deleting a subtraction data point if it does not fall within a bin corresponding to one of the one or more multi-dimensional groups defined by one or more bin boundaries.

34. The system of claim 28, wherein the processing apparatus is further operable to compare the plurality of subtraction data points of one or more groups of subtraction data points to corresponding multi-dimensional groups of clustered data points by subtracting at least a plurality of subtraction data points from corresponding multi-dimensional groups of clustered data points resulting in difference data points, and further wherein the processing apparatus is further operable to re-bin the difference data points so that they form a subset of the at least a first multi-dimensional data set.

35. The system of claim 28, wherein each data point is representative of a plurality of parameters associated with an event of a plurality of events, and further wherein the user interface is operable to allow the user to ignore at least one of the plurality of parameters when comparing the plurality of subtraction data points of one or more groups of subtraction data points to corresponding multi-dimensional groups of clustered data points.

36. The system of claim 28, wherein the processing apparatus is further operable to group the plurality of data points into one or more multi-dimensional groups of clustered data points by:
providing multiple bins, wherein each of the multiple bins has a data point of the plurality of data points recognized as a center point for the bin, and further wherein each bin is defined by one or more bin boundaries associated with the at least two parameters;
continuing to bin further data points of the plurality of data points, wherein the plurality of data points are continued to be binned by:
evaluating, for each data point, the distance between the data point and the center points of defined multiple bins to identify the closest defined bin;
if the data point fits within the closest defined bin, then adding the data point to the closest defined bin; and
if the data point does not fit within the closest defined bin, then recognizing the data point as a center point of another bin defined by one or more bin boundaries associated with the at least two parameters.

37. The system of claim 36, wherein the processing apparatus is further operable to provide multiple bins by:
recognizing a first data point of the plurality of data points as a center point of a first bin defined by one or more bin boundaries associated with the at least two parameters;
continuing to evaluate one or more other data points of the plurality of data points to determine whether the one or more other data points fit within the first bin, wherein continuing to evaluate other data points comprises:
if one of the one or more other data points fits within the first bin defined by the one or more bin boundaries, then adding the data point to the first bin resulting in a multi-dimensional data cluster of data points; and
if one of the one or more other data points does not fit within the first bin, then recognizing the data point as a center point of a second bin defined by one or more boundaries associated with the at least two parameters.

38. The system of claim 36, wherein the processing apparatus is further operable to:
determine whether a data point has the same coordinates as a data point already in one of the multiple bins;
if the data point does not have the same coordinates, then adding the data point to the bin as an additional data point; and
if the data point does have the same coordinates, then increasing the weight of the data point already the one of the multiple bins.

39. The system of claim 28, wherein the at least a first and second multi-dimensional data sets comprise data generated by analysis of gene expression or protein expression microarrays or other non-array processes.

40. The system of claim 28, wherein the at least a first and second multi-dimensional data sets comprise data generated by at least one of flow cytometry analysis; imaging analysis; microarray analysis; and gel analysis.

41. The system of claim 40, wherein the at least a first and second multi-dimensional data sets comprise data generated by multi-spectral imaging analysis.

42. The system of claim 40, wherein the at least a first and second multi-dimensional data sets comprise data generated by flow cytometry analysis.

43. The system of claim 42, wherein the processing apparatus is further operable to identify rare cell subpopulations in the at least one multi-dimensional data set.

44. The system of claim 42, wherein the processing apparatus is further operable to identify cell subpopulations in at least one of the multi-dimensional data sets.

45. The system of claim 44, wherein the system further comprises a cell sorting apparatus, wherein the cell sorting apparatus comprises sort gates set as a function of the identified cell subpopulations.

46. The system of claim 44, wherein the system further comprises a cell sorting apparatus, wherein the cell sorting apparatus comprises at least one lookup table or embedded algorithm for use in making real-time sort decisions when running cell containing samples through the cell sorting apparatus, wherein the embedded algorithm or the look-up table comprises information determined using the identified cell subpopulations as training sets for one or more subsequent multivariate statistical classifiers.

47. The system of claim 46, wherein the one or more multivariate statistical classifiers comprises at least one of discriminant function analysis and logistical regression analysis.

48. A computer implemented method for use in analyzing similarities or differences between two or more multi-dimensional data sets comprising cell data, the method comprising:
providing two or more multi-dimensional data sets;
providing a plurality of data points for at least a first of the two or more multi-dimensional data sets, wherein each data point is representative of at least two parameters associated with one of a plurality of cells;
grouping the plurality of data points into one or more multi-dimensional groups of clustered data points, wherein each of the multi-dimensional groups is defined by one or more bin boundaries associated with the at least two parameters;

providing a plurality of subtraction data points for at least a second of the two more multi-dimensional data sets, wherein each subtraction data point is representative of the at least two parameters associated with one of a plurality of cells;

grouping the plurality of subtraction data points into one or more groups of subtraction data points based on the one or more bin boundaries of the one or more multi-dimensional groups of clustered data points, wherein each of the one or more groups of subtraction data points corresponds to one of the one or more multi-dimensional groups of clustered data points; and subtracting at least a plurality of the subtraction data points from similar, not necessarily identical, data points of the one or more multi-dimensional groups of clustered data points resulting in data representative of similarities or differences between at least the first multi-dimensional data set and the second multi-dimensional data set.

49. The method of claim 48, wherein the clustered data points comprise weighted clustered data points, wherein the subtraction data points comprise weighted subtraction data points, and further wherein subtracting at least a plurality of the subtraction data points from similar, not necessarily identical, data points of the one or more multi-dimensional groups of clustered data points comprises subtracting at least a plurality of the weighted subtraction data points from the one or more multi-dimensional groups of weighted clustered data points.

50. The method of claim 49, wherein subtracting at least a plurality of the subtraction data points from similar, not necessarily identical, data points of the one or more multi-dimensional groups of clustered data points comprises:

determining, for each weighted subtraction data point, the closest weighted clustered data point within a corresponding multi-dimensional group; and subtracting the weight of the subtraction data point from the closest weighted clustered data point.

51. The method of claim 50, wherein subtracting the weight of the subtraction data point from the closest weighted clustered data point comprises:

locating one or more next closest weighted clustered data points within the corresponding multi-dimensional group if the weight of the subtraction data point is in excess of the weight of the closest weighted clustered data point; and subtracting the excess weight from the one or more next closest weighted clustered data points.

52. The method of claim 48, wherein arouping the plurality of subtraction data points into one or more groups of subtraction data points comprises:

attempting to define, for each subtraction data point, a corresponding multi-dimensional groups based on the one or more bin boundaries defining the one or more multi-dimensional groups; and deleting a subtraction data point if it does not fall within a bin corresponding to one of the one or more multi-dimensional groups defined by one or more bin boundaries.

53. The method of claim 48, wherein subtracting at least a plurality of the subtraction data points from similar, not necessarily identical, data points of the one or more multi-dimensional groups of clustered data points results in difference data points, wherein the method further comprises re-binning the difference data points so that they form a subset of the at least the first multi-dimensional data set, and re-analyzing or displaying the subset.

54. The method of claim 48, wherein grouping the plurality of data points into one or more multi-dimensional groups of clustered data points comprises:

providing multiple bins, wherein each of the multiple bins has a data point of the plurality of data points recognized as a center point for the bin, and further wherein each bin is defined by one or more bin boundaries associated with the at least two parameters;

continuing to bin further data points of the plurality of data points, wherein continuing to bin further data points comprises:

evaluating, for each data point, the distance between the data point and the center points of defined multiple bins to identify the closest defined bin;

if the data point fits within the closest defined bin, then adding the data point to the closest defined bin; and if the data point does not fit within the closest defined bin, then recognizing the data point as a center point of another bin defined by one or more bin boundaries associated with the at least two parameters.

55. The method of claim 54, wherein the distance is calculated using a Euclidean distance calculation.

56. The method of claim 54, wherein the distance is calculated using a Manhattan distance calculation.

57. The method of claim 54, wherein providing multiple bins comprises:

recognizing a first data point of the plurality of data points as a center point of a first bin defined by one or more bin boundaries associated with the at least two parameters; and continuing to evaluate one or more other data points of the plurality of data points to determine whether the one or more other data points fit within the first bin, wherein continuing to evaluate other data points comprises:

if one of the one or more other data points fits within the first bin defined by the one or more bin boundaries, then adding the data point to the first bin resulting in a multi-dimensional group of data points; and if one of the one or more other data points does not fit within the first bin, then recognizing the data point as a center point of a second bin defined by one or more boundaries associated with the at least two parameters.

58. The method of claim 54, wherein the method further comprises:

determining whether a data point has the same coordinates as a data point already in one of the multiple bins;

if the data point does not have the same coordinates, then adding the data point to the bin as an additional data point; and if the data point does have the same coordinates, then increasing the weight of the data point already in the one of the multiple bins.

59. The method of claim 48, wherein subtracting at least a plurality of the subtraction data points from similar, not necessarily identical, data points of the one or more multi-dimensional groups of clustered data points results in a difference data set, and further wherein the method comprises comparing grouped data of another multi-dimensional data set to the difference data set.

60. The method of claim 48, wherein the method further comprises allowing a user to define at least one bin boundary associated with one of the at least two parameters.

61. The method of claim 60, wherein the method further comprises defining at least one bin boundary associated with one of the at least two parameters using a user-supplied multiplier for a fraction of a region of interest within the entire range for the parameter or using a fixed percentage factor relative to an entire range for the parameter.

62. The method of claim 48, wherein subtracting the plurality of subtraction data points from the one or more multi-dimensional groups of clustered data points comprises identifying rare cell subpopulations in at least one multi-dimensional data set.

63. The method of claim 48, wherein subtracting the plurality of subtraction data points from the one or more multi-dimensional groups of clustered data points comprises identifying cell subpopulations in at least one of the two or more multi-dimensional data sets.

64. The method of claim 63, wherein the method further comprises using the identified cell subpopulations to set sort gates on a cell sorting apparatus to isolate such cell subpopulations of a flow of cells provided therethrough.

65. The method of claim 63, wherein the method further comprises using the identified cell subpopulations as training sets for one or more subsequent multivariate statistical classifiers.

66. The method of claim 65, wherein the one or more multivariate statistical classifiers comprises discriminant function analysis or logistical regression analysis.

67. The method of claim 65, wherein the method further comprises using results from the one or more multivariate statistical classifiers to generate lookup tables or embedded algorithms for use in making real-time sort decisions when running cell containing samples through a cell sorting apparatus.

* * * * *

UNITED STATES PATENT AND TRADEMARK OFFICE
CERTIFICATE OF CORRECTION

PATENT NO. : 7,043,500 B2
APPLICATION NO. : 10/132090
DATED : May 9, 2006
INVENTOR(S) : Leary It is certified that error appears in the above-identified patent and that said Letters Patent is hereby corrected as shown below:

On the TITLE page, ITEM (73), Assignee, please delete "Syxtem" and insert --System--;

In column 31, line 49, claim 52, please delete "arouping" and insert --grouping--;

In column 31, line 53, claim 52, please delete "groups" and insert --group--.

Signed and Sealed this

Seventeenth Day of October, 2006

JON W. DUDAS
*Director of the United States Patent and Trademark Office*